(12) United States Patent
Walsdorff et al.

(10) Patent No.: US 7,495,132 B2
(45) Date of Patent: Feb. 24, 2009

(54) CATALYTICALLY ACTIVE COMPOSITION AND THE USE THEREOF IN DEHYDRATION METHODS

(75) Inventors: Christian Walsdorff, Ludwigshafen (DE); Thorsten Johann, Limburgerhof (DE); Beatrice Roessler, Bad Duerkheim (DE); Hartmut Hibst, Schriesheim (DE); Joaquim Henrique Teles, Otterstadt (DE); Sebastian Storck, Mannheim (DE); Jens Klein, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 120 days.

(21) Appl. No.: 10/587,191

(22) PCT Filed: Jan. 28, 2005

(86) PCT No.: PCT/EP2005/000867

§ 371 (c)(1),
(2), (4) Date: Jul. 25, 2006

(87) PCT Pub. No.: WO2005/073157

PCT Pub. Date: Aug. 11, 2005

(65) Prior Publication Data

US 2007/0167318 A1    Jul. 19, 2007

(30) Foreign Application Priority Data

Jan. 30, 2004  (DE) ................. 10 2004 004 801
Sep. 8, 2004   (DE) ................. 10 2004 043 495

(51) Int. Cl.
*C07C 45/65*  (2006.01)
*B01J 23/42*  (2006.01)

(52) U.S. Cl. .................. 568/343; 568/388; 502/339
(58) Field of Classification Search ............... 502/339; 568/343, 388

See application file for complete search history.

(56) References Cited

U.S. PATENT DOCUMENTS

| | | |
|---|---|---|
| 3,364,264 A | 1/1968 | Hardman et al. |
| 3,940,329 A | 2/1976 | Wilhelm |
| 4,139,495 A | 2/1979 | Antos |
| 4,246,202 A | 1/1981 | Cihonski |
| 4,298,755 A | 11/1981 | Daniel et al. |
| 4,518,796 A | 5/1985 | Aoshima et al. |
| 5,070,061 A | 12/1991 | Langerbeins |
| 6,127,310 A | 10/2000 | Brown et al. |
| 6,337,424 B1 | 1/2002 | Karim et al. |
| 6,433,229 B1 | 8/2002 | Fischer et al. |
| 2001/0001805 A1 | 5/2001 | Brown et al. |
| 2003/0013904 A1 | 1/2003 | Chaturvedi et al. |

FOREIGN PATENT DOCUMENTS

| | | |
|---|---|---|
| GB | 1 340 612 | 12/1973 |
| JP | 49127909 | 12/1994 |

OTHER PUBLICATIONS

Wenkin, Mireille et al., "The role of bismuth as promoter in Pd-Bi catalysts for the selective oxidation of glucose to gluconate", Journal of Molecular Catalysis A: Chemical, vol. 180, No. 1-2, pp. 141-159, 2002.

Alardin, F. et al., "Bisumuth-promoted palladium catalysts for the selective oxidation of glyoxal into glyoxalic acid", Applied Catalysis A: General, vol. 215, No. 1-2, pp. 125-136, 2001.

Takita, Y. et al., "Promotion effects of an extremely low concentration of noble metals supported onto Bi2 MO3O12 on the partial oxidation of iso-butane", Applied catalysis A: General, vol. 225, No. 1-2, pp. 215-221, 2002.

Ruth, K. et al., "Mo-V-Nb Oxide Catalysts for the Partial Oxidation of Ethane", Journal of Catalysis, vol. 175, No. 1, pp. 16-26, 1998.

Theissen, R. J. et al., "A New-Method for the Preparation of α, β-Unsaturated Carbonyl Compounds", J. Org. Chem., vol. 36, No. 6, pp. 752-757, 1971.

*Primary Examiner*—Sikarl A Witherspoon
(74) *Attorney, Agent, or Firm*—Oblon, Spivak, McClelland, Maier & Neustadt, P.C.

(57) ABSTRACT

The present invention relates to a catalytically active composition comprising as active component
 Pd and Bi and
 at least one element selected from the group (a) consisting of Rh, Au, Sb, V, Cr, W, Mn, Fe, Co, Ni, Na, Cs and Ba,
or
 Pd, Rh and Bi and
 optionally an element selected from the group (a') consisting of Au, Sb, V, Cr, W, Mn, Fe, Co, Ni, Pt, Cu, Ag, Na, Cs, Mg, Ca and Ba.

The present invention further provides a process for dehydrogenating hydrocarbons, preferably oxo-functionalized hydrocarbons such as cyclopentanone, cyclohexanone and isovaleraldehyde, using the catalytically active composition.

12 Claims, 4 Drawing Sheets

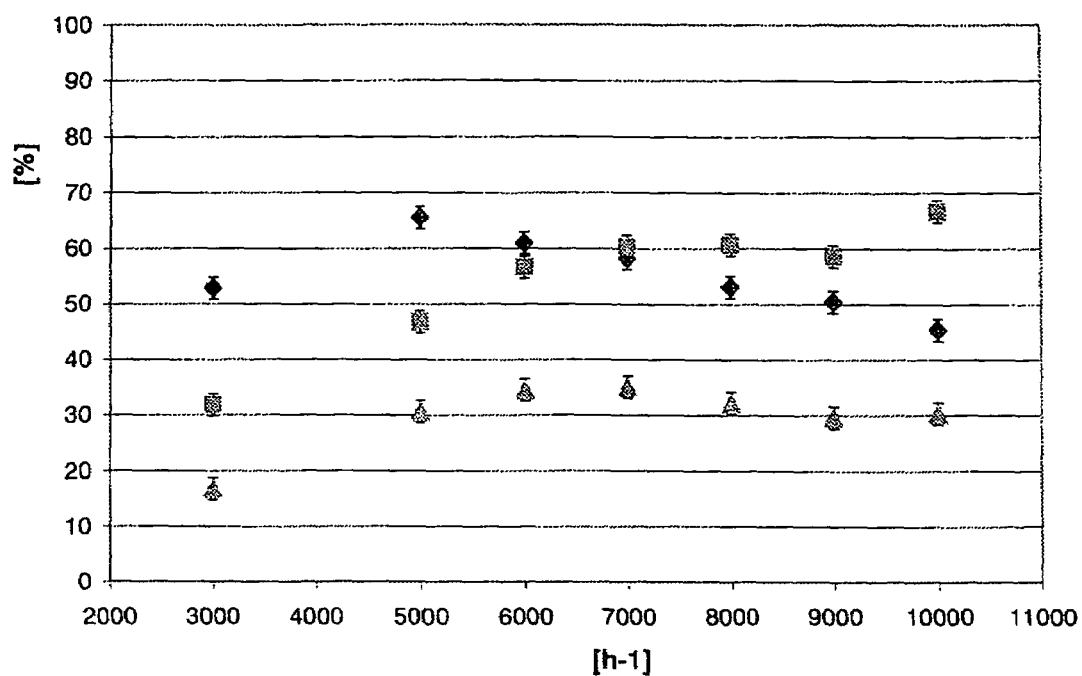
Figure 1: Dependence of conversion, selectivity and yield on the GHSV

Figure 2: Dependence of conversion, selectivity and yield on the oxygen partial pressure
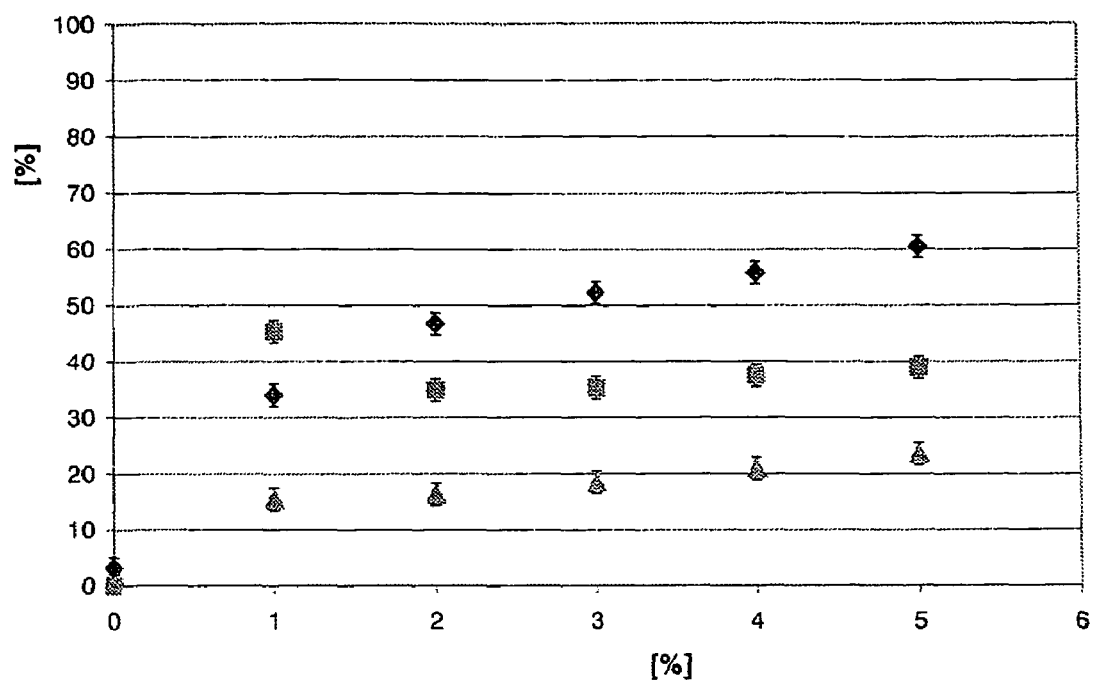

Figure 3: Dependence of conversion, selectivity and yield on the reactor temperature
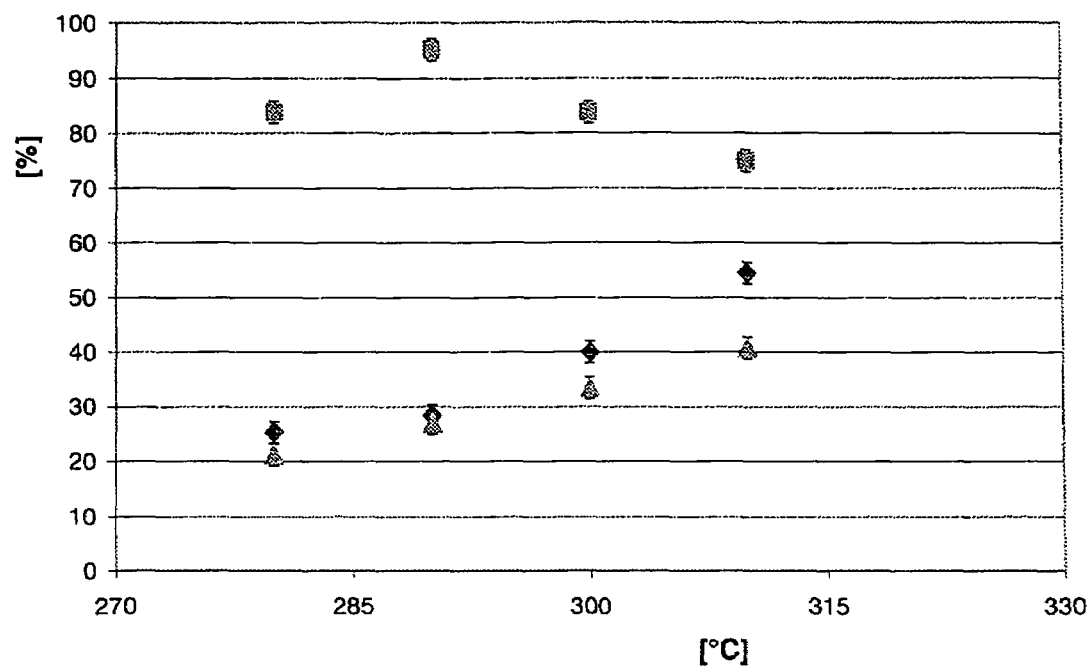

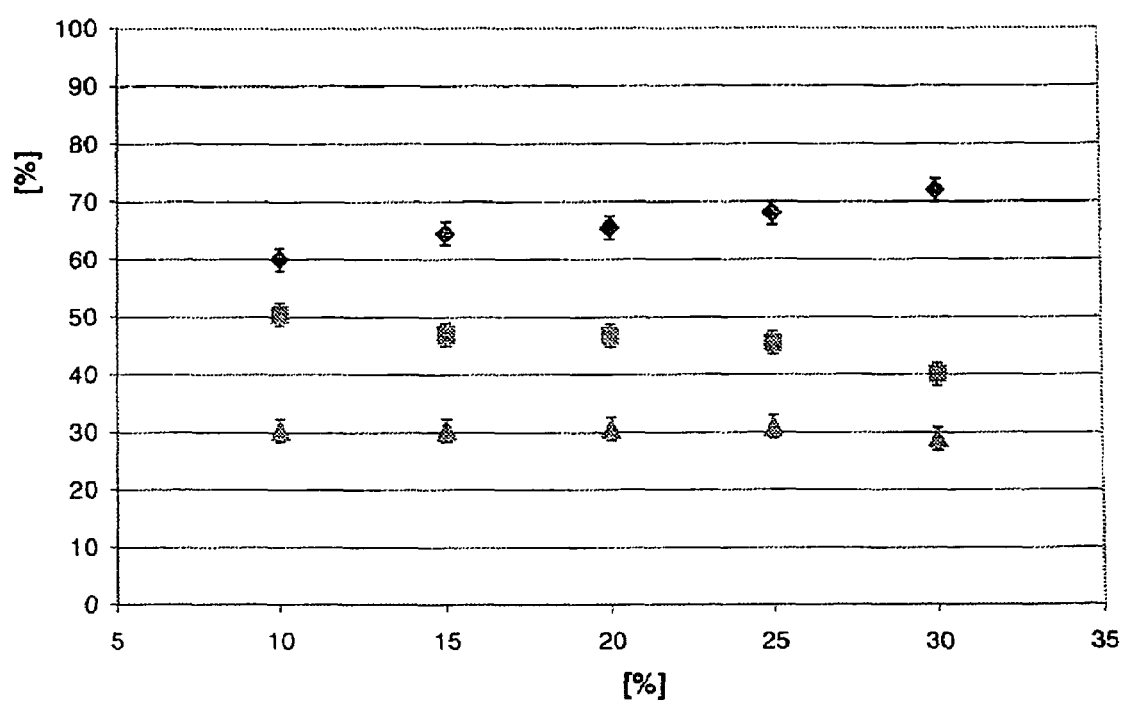
Figure 4: Dependence of conversion, selectivity and yield on the water content

CATALYTICALLY ACTIVE COMPOSITION AND THE USE THEREOF IN DEHYDRATION METHODS

DESCRIPTION

The present invention relates to a catalytically active composition which comprises as active component Pd and Bi or Pd, Rh and Bi and at least one element selected from the group (a) or from the group (a') and may have been applied to at least one support material. Furthermore, the invention relates to a process for preparing the catalytically active compositions in question and to the use of these for the dehydrogenation of hydrocarbons.

75% of all synthesized compounds are nowadays produced using catalysts. Dehydrogenation processes carried out in industry, for example the conversion of preferably short-chain alkanes into alkenes both oxidatively and in the absence of oxygen, can also no longer be implemented in industry without the use of catalysts. The conversion of ethylbenzene into styrene or isobutyric acid into methacrylic acid using suitable catalysts are important industrial dehydrogenation processes. However, few of these dehydrogenation processes utilize oxo-functionalized hydrocarbons as starting materials, since the risk of dehydrogenation/oxidation at the oxo function is greatest here. For this reason, processes for the (oxy) dehydrogenation of saturated aldehydes or alcohols to form the corresponding unsaturated products in economical yields and under economically feasible process conditions are very rare. An exception is the dehydrogenation of carboxyl-functional hydrocarbons, since in this case no further oxidation can occur at the carboxyl group. However, there is a risk of decarboxylation in this case.

The dehydrogenation of alkanes is generally carried out using catalyst systems based on multimetal mixed oxides. For example, U.S. Pat. No. 5,070,061 describes the use of active compositions comprising vanadium-based oxides, e.g. V/MgO catalysts, VPO materials, V—Sb mixed oxides. A further class known from the literature comprises catalytically active compounds based on iron phosphate. As described in U.S. Pat. No. 4,298,755, iron phosphates are used not only in the customary ODH (oxy-dehydrogenation) or DH (dehydrogenation) reactions but also in reactions such as the conversion of isobutyraldehyde into methacrolein or of isobutyric acid into methacrylic acid. Catalytically active compounds based on noble metals in elemental (reduced) or in oxidic form are used only rarely in dehydrogenation reactions of oxo-functionalized hydrocarbons. Thus, the preparation of crotonaldehyde is at present generally carried out in the liquid phase by aldol condensation of acetaldehyde via acetaldol as intermediate. However, since crotonaldehyde is an economically important starting material, for example in the synthesis of vitamin E, for the preparation of the preservative sorbic acid and for the synthesis of the lubricant 3-methoxybutanol, there is great interest in developing a suitable catalyst by means of which the synthesis of crotonaldehyde can be carried out more economically.

GB 1,340,612 describes the conversion of saturated ketones into the corresponding alpha,beta-unsaturated ketones in solution over homogeneous noble metal catalysts. However, homogeneous catalyzed processes have the disadvantage of a complicated separation of the catalyst from the reaction mixture compared to heterogeneously catalyzed processes.

U.S. Pat. No. 3,364,264 describes the dehydrogenation of carbonyl compounds in the gas phase to form the corresponding alpha,beta-unsaturated carbonyl compounds in the presence of oxygen over oxidic catalysts.

JP 49127909 describes the conversion of butanone into butenone in the gas phase in the presence of water vapor over catalysts comprising iron oxide. At 500° C., the conversion is 5.5% and the selectivity is 83%.

U.S. Pat. No. 6,433,229 describes the dehydrogenation of cyclic ketones such as cyclopentanone in the gas phase in the absence of oxygen over various dehydrogenation catalysts. However, the catalyst activity decreases relatively quickly and the catalyst has to be regenerated frequently by burning off residues. In addition, the process has to be carried out at temperatures above 400° C.

Furthermore liquid-phase dehydrogenations for preparing α,β-unsaturated ketones are known. Here, salts and complexes of Pd, Rh and Pt are used as catalysts. Thus, J. Org. Chem. 36, 752 (1972) describes the liquid-phase dehydrogenation of cyclohexanone to 2-cyclohexenone in a yield of 90% over a $PdCl_2$ or $CuCl_2$ catalyst.

It is accordingly an object of the present invention to provide suitable catalytically active compositions for the gas-phase dehydrogenation of hydrocarbons, in particular of oxo-functionalized hydrocarbons such as acyclic and cyclic aldehydes and ketones.

This object is achieved by catalytically active compositions comprising as active component Pd and Bi and at least one element selected from the group (a) consisting of Rh, Au, Sb, V, Cr, W, Mn, Fe, Co, Ni, Na, Cs and Ba.

The object is also achieved by catalytically active compositions comprising as active component Pd, Rh and Bi and at least one element selected from the group (a') consisting of Au, Sb, V, Cr, W, Mn, Fe, Co, Ni, Pt, Cu, Ag, Na, Cs, Mg, Ca and Ba.

A catalytically active composition which has been found to be advantageous is a composition comprising an active component having the following formula:

$$Pd_aX_bBi_cY_dZ_e$$

where X=Rh and/or Au;
Y=Au, Rh, Pt, Ag, Cr, Co, Cu, W, V, Fe or Mn;
Z=Au, Rh, Pt, Ag, Cr, Co, Cu, W, V, Fe or Mn;

and the indices a, b, c, d and e indicate the mass ratios of the respective elements. Index a is in the range $0.1 \leq a \leq 3$, index b is in the range $0 \leq b \leq 3$, index c is in the range $0.1 \leq c \leq 3$, index d is in the range $0 \leq d \leq 3$ and index e is in the range $0 \leq e \leq 3$.

In one embodiment, the invention provides a catalytically active composition of the above formula in which Y=Rh or Au and Rh and Au are present as X-ray-amorphous constituents or as oxidic constituents.

In a preferred embodiment, the present invention provides catalytically active compositions of the abovementioned formula in which X=Rh and Y and Z are selected from among Ag, Co and Pt.

In a further embodiment, the present invention provides a catalytically active composition of the abovementioned formula in which the indices b and e are each 0 and Y=Au or Rh, i.e. a $Pd_aBi_cAu_d$ or $Pd_aBi_cRh_d$ compound as catalytically active composition.

In a further embodiment, the present invention provides a catalytically active composition of the abovementioned formula in which the indices d and e are each 0 and X=Rh, i.e. a $Pd_aRh_bBi_c$ compound as catalytically active composition.

Furthermore, the present invention provides catalytically active compositions of the abovementioned formula in which the indices b, d and e are each 0 and the catalytically active composition is thus a $Pd_aBi_c$ compound.

Furthermore, the present invention provides catalytically active compositions of the abovementioned formula in which the index d=0 and X=Rh and Z=Ag and the catalytically active composition is thus a $Pd_aRh_bBi_cAg_e$ compound.

Furthermore, the present invention provides catalytically active compositions of the abovementioned formula in which the index d=0 and X=Rh and Z=Pt and the compound is thus a $Pd_aRh_bBi_cPt_e$ compound.

Furthermore the present invention provides catalytically active compositions of the abovementioned formula in which the indices b and d are each 0 and Z=Co and the compound is thus a $Pd_aBi_cCo_e$ compound.

All catalytically active compositions described above can be used both as fully-active catalysts and as support catalysts. In the case of support catalysts, the active component of the catalytically active composition is applied to a suitable support material.

Accordingly, the present invention also provides catalytically active compositions as described above in which the active component has been applied to at least one support material.

Any support material known to those skilled in the art can be used for the purposes of the present invention. The supports can also have all geometries known to those skilled in the art, for example rods, rings, extrudates, spheres, granules, powder, pellets, etc.

Accordingly, the present invention also provides a catalytically active composition as described above in which the support material or materials is/are selected from the group consisting of silicon carbides, silicon nitrides, carbonitrides, oxonitrides, oxocarbides, bismuth oxide, titanium oxide, zirconium oxide, boron nitride, aluminum oxide, silicates, aluminosilicates, zeolitic and zeolite-analogous materials, steatite, activated carbon, metal meshes, stainless steel meshes, steel meshes and mixtures of two or more of the abovementioned support materials.

Particular preference is given to using steatite or silicon carbide as support material for the purposes of the present invention.

The ceramic supports mentioned can be in the form of materials having a high surface area, for example greater than 100 m$^2$/g. However, preference is given to using supports having low surface areas (less than 100 m$^2$/g), particularly preferably supports having very low surface areas (less than 20 m$^2$/g), for the purposes of the present invention. Apart from the pure oxidic, nitridic or carbidic supports, it is also possible to use support materials into which basic components, for example magnesium oxide (MgO), calcium oxide (CaO), barium oxide (BaO) or other alkali metal components or alkaline earth metal components, have been mixed or in which these are present.

For the purposes of the present invention, particular preference is given to using support materials having a low intrinsic porosity (specific surface area <20 m$^2$/g) or without intrinsic porosity.

For the purposes of the present invention, the total loading of the support material or materials with at least one active component of the catalytically active composition of the abovementioned type is in the range from 0.1 to 20% by weight, preferably in the range from 8 to 15% by weight and more preferably in the range from 0.1 to 7% by weight and particularly preferably in the range from 0.5 to 4% by weight.

Accordingly, the present invention also provides a catalytically active composition of the type in question in which the total loading of the support material or materials with an active component is less than 20% by weight.

If steatite is used as support material for the purposes of the present invention, a total loading of active component of 2-4% by weight, in particular 3% by weight, is preferably employed.

The index a is in the range $0.1 \leq a \leq 3$, preferably $0.5 \leq a \leq 2$ and particularly preferably $0.75 \leq a \leq 1.5$. The index b is in the range $0 \leq b \leq 3$, preferably $0.5 \leq b \leq 2$ and particularly preferably $0.75 \leq b \leq 1.5$. The index c is in the range $0.1 \leq c \leq 3$, preferably $0.5 \leq c \leq 2$, particularly preferably $0.75 \leq c \leq 1.5$. In one embodiment of the invention in which the total loading of the support material with the abovementioned active component is 3% by weight, based on the weight of the support material, the indices additionally indicate the percentages by weight of the individual elements, based on the respective support material. In further preferred embodiments, in which the total loading of the support material or materials is up to 20% by weight, based on the weight of the support material, the analogous values of the indices converted to the respective total loading chosen apply. Thus, in a preferred embodiment of the invention, the indices a-c indicate the weight ratios of the active metals concerned, subject to the additional boundary condition that the sum of the indices a+b+c=3.

In a particularly preferred embodiment of the present invention, the ratio of the indices a, b and c is as follows: c=a+b or c=(a+b)/2, with the indices indicating the mass ratios of the individual elements or the percentages by weight of the individual elements, based on the mass of the support.

The index d is, for the purposes of the present invention, in the range $0 \leq d \leq 1$, preferably $0.0001 \leq d \leq 0.5$ and particularly preferably $0.01 \leq d \leq 0.1$. The index e in the abovementioned formula is generally in the range $0 \leq e \leq 1$, preferably $0.0001 \leq e \leq 0.5$ and particularly preferably $0.01 \leq e \leq 0.1$, with the indices indicating the mass ratios of the respective elements or percentages by weight of the respective elements, based on the mass of the support.

Catalytically active compositions which have been found to be particularly advantageous are compositions comprising an active component having one of the following formulae:

$Pd_{0.5-1.0}Rh_{0.5-1.25}Bi_{1.25-1.75}Ag_{0.05-0.15}$ $Pd_{0.5-1.0}Rh_{1.0-1.5}Bi_{0.75-1.25}Pt_{0.01-0.1}$ $Pd_{0.25-0.5}Rh_{1.75-2.5}Bi_{0.25-0.5}Co_{0.01-0.1}$ $Pd_{0.5-1.25}Rh_{0.5-1.25}Bi_{0.75-1.5}Cr_{0.01-0.1}$ $Pd_{1.0-1.75}Rh_{0.25-0.75}Bi_{0.75-1.5}Pt_{0.0-0.15}Co_{0.01-0.1}$ $Pd_{1.0-1.75}Rh_{0.25-0.75}Bi_{0.75-1.5}Pt_{0.05-0.15}$ $Pd_{0.5-1.0}Rh_{1.0-1.75}Bi_{0.5-1.25}Ag_{0.03-0.15}Ca_{0.02-0.1}$ $Pd_{0.4-1.0}Rh_{1.0-1.75}Bi_{0.75-1.25}Ag_{0.03-0.15}$ $Pd_{1.25-1.75}Rh_{1.25-1.75}Co_{0.005-0.02}$ $Pd_{0.4-1.0}Rh_{1.0-1.75}Bi_{0.75-1.25}$ $Pd_{0.15-2.25}Rh_{0-2.5}Bi_{0.15-2.75}$

Here, the indices are the mass ratios of the individual elements. Particular preference is given to compositions of the above formulae in which, in addition, a+b+c=3.

Examples of catalytically active compositions which have been found to be particularly advantageous comprise an active component of one of the following formulae:

$Pd_{0.75}Rh_{0.75}Bi_{1.5}Ag_{0.1}$;

$Pd_{0.75}Rh_{1.25}Bi_1Pt_{0.05}$;

$Pd_{0.325}Rh_{2.25}Bi_{0.375}Co_{0.05}$;

$Pd_{0.85}Rh_{0.85}Bi_{1.25}Cr_{0.05}$;

$Pd_{1.4}Rh_{0.375}Bi_{1.25}Pt_{0.1}Co_{0.05}$;

$Pd_{1.4}Rh_{0.375}Bi_{1.25}Pt_{0.1}$ $Pd_{0.8}Rh_{1.3}Bi_{0.85}Ag_{0.05}Ca_{0.05}$, $Pd_{0.6}Rh_{1.33}Bi_{1}Ag_{0.08}$ $Pd_{1.5}Bi_{1.5}Co_{0.01}$ or $Pd_{0.6}Rh_{1.33}Bi_{1}$

Catalytically active compositions which have been found to be particularly advantageous are, for example, compositions comprising an active component of one of the following formulae $Pd_{0.75\%}Rh_{0.75\%}Bi_{1.5\%}Ag_{0.1\%}$;

$Pd_{0.75\%}Rh_{1.25\%}Bi_{1\%}Pt_{0.05\%}$;

$Pd_{0.325\%}Rh_{2.25\%}Bi_{0.375\%}Co_{0.05\%}$;

$Pd_{0.85\%}Rh_{0.85\%}Bi_{1.25\%}Cr_{0.05\%}$;

$Pd_{1.4\%}Rh_{0.375\%}Bi_{1.25\%}Pt_{0.1\%}Co_{0.05\%}$;

$Pd_{1.4\%}Rh_{0.375\%}Bi_{1.25\%}Pt_{0.1\%}$;

$Pd_{0.8\%}Rh_{1.3\%}Bi_{0.85\%}Ag_{0.05\%}Ca_{0.05\%}$;

$Pd_{0.6\%}Rh_{1.33\%}Bi_{1\%}Ag_{0.08\%}$;

$Pd_{1.5\%}Bi_{1.5\%}Co_{0.01\%}$ or $Pd_{0.6\%}Rh_{1.33\%}Bi_{1\%}$;

applied to at least one support material as described above, with the indices indicating the proportions by mass (% by weight), based on the respective support material.

Catalytically active compositions which have been found to be particularly useful for the dehydrogenation of cyclohexanone to 2-cyclohexenone are compositions of the formulae $Pd_{0.15-2.25}Rh_{0-2.5}Bi_{0.15-2.75}$ $Pd_{0.1-1.0}Rh_{1.5-3.0}Bi_{0.1-1.0}$ $Pd_{0.1-1.1}Rh_{1.0-2.6}Bi_{0.1-1.1}$ $Pd_{0.1-1.1}Rh_{1.2-2.8}Bi_{0.1-1.1}$ $Pd_{0.1-1.5}Rh_{1.0-2.99}Bi_{0.1-1.5}$ $Pd_{1.0-2.0}Rh_{0.1-1.0}Bi_{0.5-2.0}$ These are, in particular, present on steatite as support. Examples are $Pd_{0.375}Rh_{2.25}Bi_{0.375}$ $Pd_{0.6}Rh_{1.8}Bi_{0.6}$ $Pd_{0.45}Rh_{2.1}Bi_{0.45}$ $Pd_{0.5}Rh_{2.0}Bi_{0.5}$ $Pd_{1.5}Rh_{0.375}Bi_{1.125}$ Catalytically active compositions which have been found to be particularly useful for the dehydrogenation of cyclopentanone to 2-cyclopentenone are compositions of the formulae $Pd_{0.4-1.0}Rh_{1.0-1.75}Bi_{0.75-1.25}Ag_{0.03-0.15}$ $Pd_{1.25-1.75}Rh_{1.25-1.75}Co_{0.005-0.02}$ $Pd_{0.2-1.0}Bi_{0.6-1.4}Rh_{0.93-1.73}Ag_{0.01-0.20}$ $Pd_{1.0-2.0}Bi_{1.0-2.0}Co_{0.005-0.15}$ $Pd_{1.0-2.0}Bi_{1.0-2.0}Pt_{0.05-0.15}$ $Pd_{0.7-1.7}Rh_{0.3-1.5}Bi_{0.3-1.5}Co_{0.05-0.15}$ These are, in particular, present on steatite as support. Examples are $Pd_{0.6}Bi_{1}Rh_{1.33}Ag_{0.08}$ $Pd_{1.5}Bi_{1.5}Co_{0.01}$ $Pd_{1.5}Bi_{1.5}Pt_{0.1}$ $Pd_{1.2}Rh_{0.9}Bi_{0.9}Co_{0.1}$ Catalytically active compositions which have been found to be particularly useful for the dehydrogenation of isovaleraldehyde to prenal are compositions of the formulae $Pd_{0.5-2.0}Rh_{0.1-1.1}Bi_{0.5-2.0}$ $Pd_{1.0-2.0}Rh_{0.1-1.0}Bi_{0.5-2.0}$ $Pd_{1.0-2.5}Rh_{0.01-0.5}Bi_{0.5-1.75}$ $Pd_{0.1-1.5}Rh_{0.5-1.75}Bi_{1.25}Pt_{0.001-0.1}$ These are, in particular, present on steatite as support. Examples are $Pd_{1.2}Rh_{0.6}Bi_{1.2}$ $Pd_{1.5}Rh_{0.375}Bi_{1.125}$ $Pd_{1.8}Rh_{0.15}Bi_{1.05}$ $Pd_{0.75}Rh_{1}Bi_{1.25}Pt_{0.05}$ In a particularly preferred embodiment, the above-described active components are applied to steatite, silicon carbide or a mixture of the two as support materials.

Furthermore, the present invention also provides a process for preparing a catalytically active composition comprising an active component of the abovementioned type as all-active catalyst.

In principle, all methods known to those skilled in the art for preparing all-active catalysts can be used for this purpose. The preferred method of preparation is the chemical process of precipitation. Here, one, two or more elements selected from the group of the active components are mixed as aqueous salt solutions and then coprecipitated in the form of their hydroxides or carbonates. An amorphous or crystalline precipitate or a gel is formed. If appropriate, the precipitate formed can be washed free of salts. The resulting product is dried in a next process step. If appropriate, the dried solid can be additionally milled to achieve better homogenization of the product. Likewise, the solid can be shaped if appropriate; in the shaping procedure, the respective product can, if appropriate, be plasticized by kneading and extruded to form extrudates, or can also, after addition of auxiliaries, be pressed to form pellets. The dried product is subsequently calcined.

The calcined product can, if appropriate, be activated and, if appropriate, be tested to determine its catalytic properties such as selectivity and activity and also stability. Testing can be carried out by all methods known to those skilled in the art, for example test use of a catalyst in selected reactions and analysis of its catalytic properties.

Accordingly, the present invention also provides a process for preparing a catalytically active composition of the abovementioned type comprising at least one active component, which process comprises at least the following steps:
(i) precipitation of at least one active component from a solution comprising one of its salts;
(ii) drying of the product prepared in step (i);
(iii) calcination of the product dried in step (ii);
(iv) if appropriate, testing of the product calcined in step (iii).

The present invention likewise provides a process for preparing a supported catalytically active composition comprising an active component applied to at least one support material.

In general, such supported catalysts comprising an active component of the abovementioned type can be prepared using all methods of preparation known for this purpose to those skilled in the art.

For the purposes of the present invention, particular preference is given to impregnation of the support body below the water uptake of the support ("incipient wetness") or adsorption from excess solution or application of thin layers to ceramic support materials as possible synthetic routes for preparing supported catalysts.

In general, the elements of the active component are used as thermally unstable salts, for example nitrates, acetates, carbonates or hydroxides, in all the methods mentioned. In the case of impregnation from excess solution, the support is immersed in the solution comprising the elements of the respective active component in the form of their anions and treated under precisely defined conditions in terms of concentration, mixing, temperature and time. To increase the effectiveness of the impregnation, the air in the pores of the support may, if appropriate, be removed by evacuation or the support can be treated with gas prior to impregnation. The impregnation step is generally followed by a drying and calcination step.

In the synthetic route involving application of thin layers to ceramic support materials, the respective precursor solutions can be applied individually in succession or preferably as a mixture to the support. In this cases preference is given to using the thermally unstable anions of the respective elements which are present in the active component according to the above explanations. Application can be carried out by simple delivery from a pipette or by spraying, spray-freeze drying and all other techniques known to those skilled in the art for this purpose. It is likewise possible to apply thin layers of the respective elements of the catalytically active composition to a desired support by means of spray-freeze drying as described in DE 102 11 260.6.

The application of the precursor solution is generally followed by a drying step. In this drying step, the materials are dried at temperatures of from 40° C. to 150° C. for from 30 minutes to 24 hours. Preference is given to drying the materials at 80° C. for 3 hours. Preference is likewise given to freeze drying the materials in vacuo or under reduced pressure.

The drying step is generally followed by a calcination step. Calcination is generally understood to be a heat treatment in an oxidizing atmosphere at temperatures which are generally above the future use temperatures of the catalytically active composition. For the purposes of the present invention, the materials are heated at a heating rate in the range from 0.25° C./min to 10° C./min over a period of from 1 to 100 hours to a final temperature of from 200° C. to 1200° C. and maintained at the chosen temperature for from 30 minutes to 150 hours. For the purposes of the present invention, a ramp of 3° C./min, a final temperature of 550° C. and a hold time of 3 hours are preferred. Possible calcination atmospheres are air, $N_2$, welding gas ($H_2$ in $N_2$, for example 5% of $H_2$ in $N_2$), vacuum or reactive gases ($Cl_2$, $NH_3$ and others) or in vacuo or under reduced pressure. The calcination is preferably carried out in air or $N_2$.

Accordingly, the invention also provides a process for preparing a catalytically active composition comprising at least one active component applied to at least one support material, which comprises at least the following steps:
($\alpha$) application of a solution comprising at least one active component to at least one support material;
($\beta$) drying of the product prepared in step ($\alpha$);
($\chi$) calcination of the product dried in step ($\beta$);
($\delta$) if appropriate testing of the product calcined in step ($\chi$).

In a further step, the catalytically active compositions in question can be tested for their catalytic properties.

The test of the catalytically active compositions prepared according to the invention can be carried out by all methods known to those skilled in the art for testing catalysts for their catalytic properties such as selectivity, activity and stability.

In general, testing of the catalytically active compositions prepared according to the present invention is carried out by installation of, for example, at least 1 ml of the material to be tested in a stainless steel reactor known to those skilled in the art. Testing is preferably carried out under inert reaction conditions. After the catalytic reaction within the reactor, the subsequent product gas analysis can be carried out by all analytical methods known for this purpose to those skilled in the art, but preferably by means of a GC/MS with an HP-5-MS column for the separation and determination of the products and starting materials.

The testing to determine the catalytic properties of the catalytically active compositions prepared can be carried out with the aid of the catalytic reaction of hydrocarbons which appear to be suitable for this purpose to those skilled in the art. The reaction of the abovementioned starting materials carried out for test purposes is not subject to any restrictions. The catalytically active compositions described in the context of the present invention can be used for nucleophilic and electrophilic substitutions, addition and elimination reactions, for double bond and skeletal isomerizations, for rearrangements and redox reactions, for alkylations, disproportionations, acylations, cyclizations, hydrations, dehydrations, aminations, hydrogenations, dehydrogenations, oxidative dehydrogenations, dehydrocyclizations, hydroxylations, oxidations, partial oxidations, ammoxidations, epoxidations and combinations of these reactions and for the targeted reaction of organic molecules.

Furthermore, the present invention also provides for the use of the catalytically active compositions for the dehydrogenation of hydrocarbons. The hydrocarbons to be dehydrogenated in the context of the present invention are not subject to any restrictions. The above-described novel catalytically active composition can in principle be used for dehydrogenating all hydrocarbons which appear suitable for this purpose to those skilled in the art.

In one embodiment of the invention, the dehydrogenation of oxo-functionalized $C_4$-hydrocarbons such as butanol, butyric acid, isobutanol, isobutyric acid and butyraldehyde is carried out.

Preference is also given to the dehydrogenation of cyclic and acyclic carbonyl compounds, particularly preferably cyclic and acyclic aldehydes and ketones, to form the corresponding alpha,beta-unsaturated carbonyl compounds. Very particularly preferred examples are the dehydrogenation of cyclopentanone to 2-cyclopentenone, of butanone to butenone, of butyraldehyde to crotonaldehyde, of cyclohexanone to 2-cyclohexenone and of isovaleraldehyde to prenal (2-methylbut-2-enal).

The present invention thus also provides a process for dehydrogenating hydrocarbons, preferably cyclic and acyclic carbonyl compounds, particularly preferably cyclic and acyclic aldehydes and ketones, to form the corresponding alpha, beta-unsaturated carbonyl compounds by bringing the hydrocarbon to be dehydrogenated into contact with the above-described catalytically active composition comprising Pd and Bi or Pd, Rh and Bi and also, if appropriate, one or more further elements from the group (a) or (a') as active component.

The dehydrogenation is particularly preferably carried out at least in the presence of oxygen.

Accordingly, the present invention also provides for the use of a catalytically active composition of the above type for the dehydrogenation of hydrocarbons in the presence of oxygen, and also provides a corresponding process.

In a further preferred embodiment of the present invention, the dehydrogenation of hydrocarbons is carried out using a catalytically active composition as described above in the presence of at least oxygen and water.

Accordingly, the present invention also provides for the use of the above-described catalytically active compositions for the dehydrogenation of hydrocarbons, wherein the dehydrogenation takes place at least in the presence of oxygen and water, and also provides a corresponding process.

The oxygen content in dehydrogenations which are carried out at least in the presence of oxygen or oxygen and water is, according to the present invention, in the range from 1% by volume to 50% by volume, preferably in the range from 1% by volume to 30% by volume and particularly preferably in the range from 1% by volume to 10% by volume or from 20 to 30% by volume, based on the total volume of the starting materials fed in.

The water content in dehydrogenations which are carried out at least in the presence of oxygen and water is in the range from 1% by volume to 50% by volume, preferably in the range from 5% by volume to 35% by volume, particularly preferably in the range from 5% by volume to 25% by volume, based on the total volume of the starting materials fed in. If appropriate, nitrogen can be fed in as balance gas in the above-described dehydrogenations.

The hydrocarbon content in dehydrogenations which are carried out as described above is in the range from 0 to 90% by volume, preferably in the range from 0.01 to 25% by volume, particularly preferably in the range from 0.1 to 4% by volume or from 15 to 25% by volume, based on the total volume of the starting materials fed in.

Accordingly, the present invention also provides for the use of a catalytically active composition as described above for the dehydrogenation of hydrocarbons at a hydrocarbon to oxygen ratio which is, for the purposes of the present invention, in the range from 3:1 to 1:20, preferably in the range from 1:1 to 1:7, particularly preferably in the range from 1:2 to 1:5, and also provides a corresponding process.

The present invention likewise provides for the use of a catalytically active composition as described above for the dehydrogenation of hydrocarbons at a hydrocarbon to water ratio in the process of the invention which is in the range from 3:1 to 1:50, preferably in the range from 1:5 to 1:40, particularly preferably in the range from 1:10 to 1:30, and also provides a corresponding process.

In general, the process conditions in the dehydrogenation to be carried out in the context of the present invention by means of a catalytically active composition are not subject to any restrictions. The catalytic compositions of the invention make dehydrogenation possible even at relatively low temperatures of significantly below 400° C. The catalyst activity remains virtually unchanged over a long period, so that reactivation is required only rarely. Furthermore, the by-products formed are predominantly gaseous by-products which are easy to separate off.

The reaction temperatures in the dehydrogenations carried out are generally in the range from 150° C. to 450° C., preferably from 200 to 450° C., particularly preferably from 250° C. to 400° C. and in particular from 250 to 360° C.

The respective space velocity (GHSV) is in the range from $100\ h^{-1}$ to $100000\ h^{-1}$, preferably from $500\ h^{-1}$ to $30000\ h^{-1}$ and particularly preferably from $3000\ h^{-1}$ to $15000\ h^{-1}$.

In the case of the dehydrogenation of cyclohexanone to 2-cyclohexenone, the following reaction conditions have, inter alia, been found to be useful: the reaction takes place at a temperature of from 360 to 450° C., preferably from 410 to 425° C. The space velocity (GHSV) is from 2000 to $9000\ h^{-1}$, preferably from 3000 to $6000\ h^{-1}$. The cyclohexanone content of the feed gas stream is from 1% by volume to 5% by volume, preferably from 3% by volume to 4% by volume. The molar cyclohexanone:oxygen ratio in the feed gas stream is about 1:2 for a maximum cyclohexanone conversion (maximum yield of 2-cyclohexenone) and is about 1:1 for maximum selectivity of 2-cyclohexenone formation. The feed gas stream can contain from 5 to 15% by volume of water, preferably about 10% by volume of water.

In the case of the dehydrogenation of cyclopentanone to 2-cyclopentenone, the following reaction conditions have, inter alia, been found to be useful: the reaction takes place at a temperature of from 370 to 410° C. The space velocity (GHSV) is, in particular, from 5000 to $7000\ h^{-1}$. The cyclopentanone content of the feed gas stream is from 3% by volume to 5% by volume. The molar cyclopentanone:oxygen ratio in the feed gas stream is about 1:2 for a maximum cyclopentanone conversion (maximum yield of 2-cyclopentenone) and is about 1:1 for maximum selectivity of 2-cyclopentenone formation. The feed gas stream can contain from 5 to 15% by volume of water.

In the case of the dehydrogenation of isovaleraldehyde to prenal, the following reaction conditions have been found to be useful: the reaction takes place at a temperature of from 270° C. to 370° C., preferably from 290° C. to 330° C. The space velocity (GHSV) is from $1000\ h^{-1}$ to $9000\ h^{-1}$, preferably from $3000\ h^{-1}$ to $6000\ h^{-1}$. The isovaleraldehyde content of the feed gas stream is from 1 to 5% by volume, preferably from 2 to 3% by volume. The molar isovaleraldehyde to oxygen ratio in the feed gas stream is from 1:1 to 1:15, preferably in the range from 1:3 to 1:8. The feed gas stream can contain from 0 to 30% by volume of water, and preferably contains from 10 to 20% by volume of water.

The dehydrogenation catalyst can be installed in the reactor as a fixed bed or, for example, can be used in the form of a fluidized bed and have an appropriate shape. Suitable shapes are, for example, crushed material, pellets, monoliths, spheres or extrudates (rods, wagon wheels, stars, rings).

A suitable type of reactor is a fixed-bed tube or shell-and-tube reactor. In these reactors, the catalyst is present as a fixed bed in a reaction tube or in a bundle of reaction tubes. The reaction tubes are usually heated indirectly by a gas, e.g. a hydrocarbon such as methane, being burnt in the space surrounding the reaction tubes or a heat transfer medium (salt bath, circulating gas, etc.) being used. The reaction tubes can also be heated electrically by means of heating sleeves. Customary internal diameters of the reaction tubes are from about 1 to 15 cm. A typical shell-and-tube dehydrogenation reactor has from about 10 to 32000 reaction tubes.

In the context of the present invention, it is possible to regenerate the catalytically active compositions of the invention when their catalytic activity drops during use in particular reactions and then to use them again.

In general, regeneration is effected by burning off the carbon deposited on the catalyst surface in the presence of oxygen. For this purpose, air or oxygen, which may be diluted with inert gases, is added to the feed gas stream comprising the compound to be dehydrogenated, with its content in the gas stream being able to be reduced to 0% by volume during the regeneration. The regeneration is carried out at a temperature of generally from 200 to 400° C.

In a variant of the regeneration, the catalytically active composition of the invention is firstly burned off at temperatures of from 200 to 400° C., preferably from 250 to 350° C., for from 1 minute to 100 hours, preferably from 10 minutes to 24 hours, particularly preferably from 30 minutes to 1.5 hours, so that the carbon deposited on the catalyst surface burns off to form carbon dioxide.

The burning-off in the context of the present invention is preferably carried out at a temperature of about 350° C. in an atmosphere comprising about 1% of oxygen in nitrogen, preferably 5% of oxygen in nitrogen, particularly preferably about 10% of oxygen in nitrogen.

After burning-off, the atmosphere surrounding the catalytically active composition is flushed with nitrogen to free it of oxygen.

As a third step of the regeneration, the catalytically active composition is treated with hydrogen. This treatment is preferably carried out at temperatures in the range from 220 to 280° C., particularly preferably from 250 to 270° C., in the presence of welding gas. Particular preference is given to using welding gas having a composition of about 3% of hydrogen in nitrogen. The hydrogen treatment is carried out for from 1 minute to 100 hours, preferably from 10 minutes to 24 hours, particularly preferably from 30 minutes to 1.5 hours.

The atmosphere surrounding the catalytically active composition is subsequently flushed free of hydrogen.

To separate water off from the organic product and unreacted starting material, the work-up of the liquid water-containing reaction product mixture preferably comprises an extraction with an organic solvent, for example dichloromethane, chloroform, methyl tert-butyl ether or ethyl acetate, or an azeotropic distillation using an organic solvent which is more volatile than the starting material and product to remove the water. The distillation of relatively high-boiling organic compounds, for example a mixture of cyclopentanone and 2-cyclopentenone, can be carried out under reduced pressure. Preference is given to adding a bottoms fluidizer, for example propylene carbonate, to reduce the thermal stress on the relatively high-boiling components to be distilled.

The present invention is illustrated by the examples below.

The examples demonstrate the preparation of various catalytically active compounds and their testing to determine catalytic properties.

Unless indicated otherwise in the individual examples, testing is carried out using 1 ml of the respective catalytically active composition.

EXAMPLE 1

Pd—Rh—Bi—Co on Steatite (Total Loading: 3% by Weight)

To synthesize material 1, 5 g of steatite (sieve fraction: 0.5-1.5 mm, Ceramtec) were placed in a porcelain dish. A mixture of aqueous solutions of the following precursors was made up in a container and mixed (cf. Table 1):

TABLE 1

| Metal salts: | Conc. [mol/l]: | µl | % by weight |
|---|---|---|---|
| Bi(NO3)3 × 5H2O | 1.25 | 197.4 | 1.0 |
| Pd(NO3)2 | 1.60 | 227.2 | 0.8 |
| Rh(NO3)3 × 2H2O | 2.00 | 313.2 | 1.3 |
| Co(NO3)2 × 6H2O | 1.00 | 43.8 | 0.1 |
| water | | 618.4 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 310° C. and a space velocity (GHSV) of 7000 $h^{-1}$ (1% of butyraldehyde, 5% of oxygen, 22% of water in nitrogen), 69.9% of butyraldehyde were reacted at a selectivity to crotonaldehyde of 56.6%. This corresponds to a yield of crotonaldehyde of 39.6%.

At 280° C. and a space velocity (GHSV) of 5000 $h^{-1}$ (1% of butyraldehyde, 4% of oxygen, 25% of water in nitrogen), 35.5% of butyraldehyde were reacted at a selectivity to crotonaldehyde of 85.4%. This corresponds to a yield of crotonaldehyde of 30.3%.

EXAMPLE 2

Pd—Rh—Bi—Ag on Steatite (Total Loading: 3% by Weight)

To synthesize material 2, 5 g of steatite (sieve fraction: 0.5-1.5 mm, Ceramtec) were placed in a porcelain dish. A mixture of aqueous solutions of the following precursors was made up in a container and mixed (cf. Table 2):

TABLE 2

| Metal salts: | Conc. [mol/l]: | µl | % by weight |
|---|---|---|---|
| Bi(NO3)3 × 5H2O | 1.25 | 296.3 | 1.5 |
| Pd(NO3)2 | 1.60 | 227.3 | 0.75 |
| Rh(NO3)3 × 2H2O | 2.00 | 188.0 | 0.75 |
| AgNO3 | 1.00 | 47.8 | 0.1 |
| water | | 641 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 310° C. and a GHSV of 10000 $h^{-1}$ (1% of butyraldehyde, 4% of oxygen, 15% of water in nitrogen), 54.4% of butyraldehyde were reacted at a selectivity to crotonaldehyde of 75.0%. This corresponds to a yield of crotonaldehyde of 40.8%.

At 300° C. and a GHSV of 6000 $h^{-1}$ (1% of butyraldehyde, 4% of oxygen, 20% of water in nitrogen), 39.2% of butyraldehyde were reacted at a selectivity to crotonaldehyde of 87.4%. This corresponds to a yield of crotonaldehyde of 34.2%.

EXAMPLE 3

Pd—Rh—Bi—Pt on Steatite (Total Loading: 3% by Weight)

To synthesize material 3, 5 g of steatite (sieve fraction: 0.5-1.5 mm, Ceramtec) were placed in a porcelain dish. A mixture of aqueous solutions of the following precursors was made up in a container and mixed (cf. Table 3):

TABLE 3

| Metal salts: | Conc. [mol/l]: | µl | % by weight |
|---|---|---|---|
| Bi(NO3)3 × 5H2O | 1.25 | 197.4 | 1 |
| Pd(NO3)2 | 1.60 | 227.2 | 0.75 |
| Rh(NO3)3 × 2H2O | 2.00 | 313.2 | 1.25 |
| EAPt(IV) [(NH4)2(EtOH)2][Pt(OH)6] | 0.500 | 26.4 | 0.05 |
| water | | 636 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 300° C. and a GHSV of 5000 $h^{-1}$ (1% of butyraldehyde, 4% of oxygen, 25% of water in nitrogen), 68.2% of butyraldehyde were reacted at a selectivity to crotonaldehyde of 59.0%. This corresponds to a yield of crotonaldehyde of 40.3%.

At 280° C. and a GHSV of 3000 $h^{-1}$ (1% of butyraldehyde, 3% of oxygen, 25% of water in nitrogen), 39.6% of butyraldehyde were reacted at a selectivity to crotonaldehyde of 82.5%. This corresponds to a yield of crotonaldehyde of 32.6%.

EXAMPLE 4

Pd—Bi—Au on Steatite (Total Loading: 3% by Weight)

To synthesize material 4, 5 g of steatite (sieve fraction: 0.5-1.5 mm, Ceramtec) were placed in a porcelain dish. A mixture of aqueous solutions of the following precursors was made up in a container and mixed (cf. Table 4):

TABLE 4

| Metal salts: | Conc. [mol/l]: | µl | % by weight |
|---|---|---|---|
| Bi(NO3)3 × 5H2O | 1.25 | 296.0 | 1.5 |
| Pd(NO3)2 | 1.60 | 227.0 | 0.75 |
| HAuCl4 × H2O | 1.00 | 196.3 | 0.75 |
| water | | 680.7 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 350° C. and a GHSV of 6000 $h^{-1}$ (1% of butyraldehyde, 4% of oxygen, 20% of water in nitrogen), 71.9% of butyraldehyde were reacted at a selectivity to crotonaldehyde of 36.5%. This corresponds to a yield of crotonaldehyde of 26.2%.

At 325° C. and a GHSV of 6000 $h^{-1}$ (1% of butyraldehyde, 4% of oxygen, 20% of water in nitrogen), 49.0% of butyraldehyde were reacted at a selectivity to crotonaldehyde of 40.3%. This corresponds to a yield of crotonaldehyde of 19.8%.

EXAMPLE 5

Pd—Bi—Au on Steatite (Total Loading: 3% by Weight)

To synthesize material 5, 5 g of steatite (sieve fraction: 0.5-1.5 mm, Ceramtec) were placed in a porcelain dish. A mixture of aqueous solutions of the following precursors was made up in a container and mixed (cf. Table 5):

TABLE 5

| Metal salts: | Conc. [mol/l]: | µl | % by weight |
|---|---|---|---|
| Bi(NO3)3 × 5H2O | 1.25 | 296.0 | 1.5 |
| Pd(NO3)2 | 1.60 | 151.4 | 0.5 |
| HAuCl4 × H2O | 1.00 | 261.7 | 1 |
| water | | 691.0 | |

The appropriate amount of the solutions is applied by means of a pipette at 4 different places on the ceramic support.

The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 350° C. and a GHSV of 6000 $h^{-1}$ (1% of butyraldehyde, 4% of oxygen, 20% of water in nitrogen), 68.6% of butyraldehyde were reacted at a selectivity to crotonaldehyde of 43.9%. This corresponds to a yield of crotonaldehyde of 30.2%.

At 315° C. and a GHSV of 6000 $h^{-1}$ (1% of butyraldehyde, 4% of oxygen, 10% of water in nitrogen), 40.3% of butyraldehyde were reacted at a selectivity to crotonaldehyde of 55.9%. This corresponds to a yield of crotonaldehyde of 22.6%.

EXAMPLE 6

Pd—Bi—Rh on Steatite (Total Loading: 3% by Weight)

To synthesize material 6, 5 g of steatite (sieve fraction: 0.5-1.5 mm, Ceramtec) were placed in a porcelain dish. A mixture of aqueous solutions of the following precursors was made up in a container and mixed (cf. Table 6):

TABLE 6

| Metal salts: | Conc. [mol/l]: | μl | % by weight |
|---|---|---|---|
| $Bi(NO3)3 \times 5H2O$ | 1.25 | 296.0 | 1.5 |
| $Pd(NO3)2$ | 1.60 | 227.0 | 0.75 |
| $Rh(NO3)3 \times 2H2O$ | 1.50 | 250.5 | 0.75 |
| water | | 627 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 325° C. and a GHSV of 10000 $h^{-1}$ (1% of butyraldehyde, 4% of oxygen, 10% of water in nitrogen), 66.6% of butyraldehyde were reacted at a selectivity to crotonaldehyde of 56.6%. This corresponds to a yield of crotonaldehyde of 37.6%.

At 290° C. and a GHSV of 10000 $h^{-1}$ (1% of butyraldehyde, 3% of oxygen, 10% of water in nitrogen), 28.7% of butyraldehyde were reacted at a selectivity to crotonaldehyde of 72.9%. This corresponds to a yield of crotonaldehyde of 20.8%.

EXAMPLE 7

Pd—Bi—Rh on Steatite (Total Loading: 3% by Weight)

To synthesize material 7, 5 g of steatite (sieve fraction: 0.5-1.5 mm, Ceramtec) were placed in a porcelain dish. A mixture of aqueous solutions of the following precursors was made up in a container and mixed (cf. Table 7):

TABLE 7

| Metal salts: | Conc. [mol/l]: | μl | % by weight |
|---|---|---|---|
| $Bi(NO3)3 \times 5H2O$ | 1.25 | 296.0 | 1.5 |
| $Pd(NO3)2$ | 1.60 | 302.7 | 1 |
| $Rh(NO3)3 \times 2H2O$ | 1.50 | 167.0 | 0.5 |
| water | | 634 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 305° C. and a GHSV of 7500 $h^{-1}$ (1% of butyraldehyde, 4% of oxygen, 20% of water in nitrogen), 68.1% of butyraldehyde were reacted at a selectivity to crotonaldehyde of 52.2%. This corresponds to a yield of crotonaldehyde of 35.5%.

At 305° C. and a GHSV of 7500 $h^{-1}$ (1% of butyraldehyde, 4% of oxygen, 20% of water in nitrogen), 68.1% of butyraldehyde were reacted at a selectivity to crotonaldehyde of 52.2%. This corresponds to a yield of crotonaldehyde of 35.5%.

EXAMPLE 8

Pd—Bi on Steatite (Total Loading: 2% by Weight)

To synthesize material 8, 5 g of steatite (sieve fraction: 0.5-1.5 mm, Ceramtec) were placed in a porcelain dish. A mixture of aqueous solutions of the following precursors was made up in a container and mixed (cf. Table 8):

TABLE 8

| Metal salts: | Conc. [mol/l]: | μl | % by weight |
|---|---|---|---|
| $Pd(NO3)2$ | 1.30 | 334.6 | 1 |
| $Bi(NO3)3 \times 5H2O$ | 1.23 | 353.7 | 1 |
| water | | 712 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 340° C. and a GHSV of 6000 $h^{-1}$ (1% of butyraldehyde, 6% of oxygen, 20% of water in nitrogen), 64.0% of butyraldehyde were reacted at a selectivity to crotonaldehyde of 43.3%. This corresponds to a yield of crotonaldehyde of 27.7%.

At 340° C. and a GHSV of 6000 $h^{-1}$ (2% of butyraldehyde, 4% of oxygen, 25% of water in nitrogen), 31.8% of butyraldehyde were reacted at a selectivity to crotonaldehyde of 73.2%. This corresponds to a yield of crotonaldehyde of 23.3%.

EXAMPLE 9

Pd—Bi—Rh—Sb on Steatite (Total Loading: 3% by Weight)

To synthesize material 9, 5 g of steatite (sieve fraction: 0.5-1.5 mm, Ceramtec) were placed in a porcelain dish. A mixture of aqueous solutions of the following precursors was made up in a container and mixed (cf. Table 9):

TABLE 9

| Metal salts: | Conc. [mol/l]: | µl | % by weight |
|---|---|---|---|
| Pd(NO3)2 | 1.25 | 184.1 | 0.5 |
| Rh(NO3)3 × 2H2O | 1.50 | 153.4 | 0.5 |
| Sb(C2H3O2)3 | 0.7275 | 158.2 | 0.25 |
| Bi(NO3)3 × 5H2O | 1.25 | 276.2 | 0.75 |
| water | | 628.0 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 350° C. and a GHSV of 3000 $h^{-1}$ (1% of butyraldehyde, 4% of oxygen, 20% of water in nitrogen), 54.0% of butyraldehyde were reacted at a selectivity to crotonaldehyde of 33.7%. This corresponds to a yield of crotonaldehyde of 18.2%.

At 350° C. and a GHSV of 6000 $h^{-1}$ (1% of butyraldehyde, 1% of oxygen, 20% of water in nitrogen), 17.5% of butyraldehyde were reacted at a selectivity to crotonaldehyde of 46.6%. This corresponds to a yield of crotonaldehyde of 8.2%.

EXAMPLE 10

Pd—Bi—Rh—Pt on Silicon Carbide (Total Loading: 3% by Weight)

To synthesize material 10, 5 g of silicon carbide (sieve fraction: 0.5-1.5 mm, Norton) were placed in a porcelain dish. A mixture of aqueous solutions of the following precursors was made up in a container and mixed (cf. Table 10):

TABLE 10

| Metal salts: | Conc. [mol/l]: | µl | % by weight |
|---|---|---|---|
| Pd(NO3)2 | 1.25 | 363.3 | 0.6 |
| Rh(NO3)3 × 2H2O | 1.50 | 666.3 | 1.33 |
| AgNO3 | 1.00 | 38.2 | 0.08 |
| Bi(NO3)3 × 5H2O | 1.25 | 197.3 | 1 |
| water | | 2734.8 | |

The appropriate amount of the solutions is applied by means of a pipette at 4 different places on the ceramic support. The material is subsequently dried at 80° C. for 16 hours in a drying oven. This is followed by calcination at 550° C. for 3 hours in a nitrogen atmosphere (6 standard l/min of $N_2$). 1 ml of the material is introduced into a stainless steel tube reactor (inert under the reaction conditions, no activity in respect of the target reaction) and heated from the outside to the reaction temperature. Product gas analysis is carried out by means of GC/MS using an HP-5-MS column for the separation and determination of the oxygen-containing compounds.

After conditioning under feed conditions (see below), the active composition reaches its optimal catalytic performance after 3-7 days.

At 260° C. and a GHSV of 5000 $h^{-1}$ (1% of butyraldehyde, 2% of oxygen, 15% of water in nitrogen), 69.9% of butyraldehyde were reacted at a selectivity to crotonaldehyde of 65.6%. This corresponds to a yield of CRA of 46.5%.

At 270° C. and a GHSV of 5000 $h^{-1}$ (1% of butyraldehyde, 4% of oxygen, 15% of water in nitrogen), 78.2% of butyraldehyde were reacted at a selectivity to crotonaldehyde of 58.3%. This corresponds to a yield of CRA of 45.6%.

EXAMPLE 11

GHSV Dependence

The material from Example 1 (installation of 1 ml of catalyst volume in the test reactor) was tested as a representative of the entire class of materials claimed at 300° C. and the feed conditions: 1% of butyraldehyde, 4% of $O_2$, 25% of $H_2O$ and $N_2$ as balance at various space velocities. The results are shown in FIG. 1. The maximum in the yield (conversion about 60%, selectivity about 60%) at space velocities of from 6000 $h^{-1}$ to 7000 $h^{-1}$ can clearly be seen. The maximum selectivity of about 68% at a conversion of about 45% is at 10000 $h^{-1}$.

EXAMPLE 12

Dependence on the Oxygen Partial Pressure

The material from Example 1 (installation of 1 ml of catalyst volume in the test reactor) was tested as a representative of the entire class of materials claimed at 300° C. and the feed conditions: 1% of butyraldehyde, 22% of $H_2O$, GHSV of 7000 $h^{-1}$ and $N_2$ as balance at various oxygen partial pressures. The results are shown in FIG. 2. The maximum in the yield at oxygen partial pressures of from 3% to 5% can clearly be seen. The maximum selectivity of about 45% at a conversion of about 35% is at 1% of $O_2$ and the maximum yield is at 5% of $O_2$ (conversion 60%, selectivity 40%, yield 24%).

EXAMPLE 13

Dependence on the Reactor Temperature

The material from Example 2 (installation of 1 ml of catalyst volume in the test reactor) was tested as a representative of the entire class of materials claimed at various temperatures and the feed conditions: 1% of butyraldehyde, 4% of $O_2$, 15% of $H_2O$, $N_2$ as balance and GHSV of 10000 $h^{-1}$. The results are shown in FIG. 3. The maximum in the yield at 310° C. (conversion about 55%, selectivity about 75%, yield about 40%) can clearly be seen. The maximum selectivity is at 290° C. (conversion about 30%, selectivity about 83%).

EXAMPLE 14

Dependence on the Water Content

The material from Example 1 (installation of 1 ml of catalyst volume in the test reactor) was tested as a representative of the entire class of materials claimed at various water contents at 300° C. and the feed conditions: 1% of butyraldehyde, 4% of $O_2$, $N_2$ as balance and GHSV of 5000 $h^{-1}$. The results are shown in FIG. 4. The maximum in the yield at 25% of $H_2O$ (conversion about 70%, selectivity about 45%, yield about 30%) can clearly be seen. The maximum selectivity is at a water content of 10% (conversion about 60%, selectivity about 50%).

EXAMPLE 15

Various Catalytically Active Compositions Comprising an Active Component on Steatite (Total Loading: 3% by Weight)

The materials 11 to 19 were prepared in a manner analogous to Example 1.

However a catalyst volume of only 0.1 ml was tested in this case.

Precursors used were the appropriate metal nitrates in aqueous solution, except in the case of Pt which was used in the form of the ethanol-amine complex.

The individual catalytic compounds, the conversion (C) achieved in the respective catalytic conversion of butyraldehyde into crotonaldehyde, the selectivity (S) achieved, the yield (Y) achieved and the respective feed composition are shown below:

11. $Pd_{0.75}Rh_{0.75}Bi_{1.5}Ag_{0.1}$/steatite, C=54.4%, S=75.0% (Y=40.8%), at 310° C., 10000 $h^{-1}$, 1% of butyraldehyde, 4% of $O_2$, 15% of $H_2O$, balance $N_2$
12. $Pd_{0.75}Rh_{0.75}Bi_{1.5}Ag_{0.1}$/steatite, C=39.2%, S=87.4% (Y=34.2%), at 300° C., 6000 $h^{-1}$, 1% of butyraldehyde, 4% of $O_2$, 20% of $H_2O$, balance $N_2$
13. $Pd_{0.75}Rh_{1.25}Bi_1Pt_{0.05}$/steatite, C=68.2%, S=59.0% (Y=40.3%), at 300° C., 5000 $h^{-1}$, 1% of butyraldehyde, 4% of $O_2$, 25% of $H_2O$, balance $N_2$
14. $Pd_{0.75}Rh_{1.25}Bi_1Pt_{0.05}$/steatite, C=39.6%, S=82.5% (Y=32.6%), at 280° C., 3000 $h^{-1}$, 1% of butyraldehyde, 3% of $O_2$, 25% of $H_2O$, balance $N_2$
15. $Pd_{0.325}Rh_{2.25}Bi_{0.375}Co_{0.05}$/steatite, C=55.4%, S=82.8% (Y=45.9%), at 300° C., 6000 $h^{-1}$, 1% of butyraldehyde, 4% of $O_2$, 25% of $H_2O$, balance $N_2$
16. $Pd_{0.85}Rh_{0.85}Bi_{1.25}Cr_{0.05}$/steatite, C=50.9%, S=90.0% (Y=45.8%), at 325° C., 10000 $h^{-1}$, 2% of butyraldehyde, 8% of $O_2$, 20% of $H_2O$, balance $N_2$
17. $Pd_{1.4}Rh_{0.375}Bi_{1.125}Pt_{0.1}Co_{0.05}$/steatite, C=54.7%, S=84.8% (Y=46.4%), at 300° C., 6000 $h^{-1}$, 1.8% of butyraldehyde, 6.7% of $O_2$, 30.3% of $H_2O$, balance $N_2$
18. $Pd_{1.4}Rh_{0.375}Bi_{1.125}Pt_{0.1}$/steatite, C=52.6%, S=95.2% (Y=50.0%), at 300° C., 6000 $h^{-1}$, 1% of butyraldehyde, 5% of $O_2$, 25% of $H_2O$, balance $N_2$
19. $Pd_{0.8}Rh_{1.3}Bi_{0.85}Ag_{0.05}Ca_{0.05}$/steatite, C=66.7%, S=63.6% (Y=42.4%), at 300° C., 6000 $h^{-1}$, 1% of butyraldehyde, 6% of $O_2$, 25% of $H_2O$, balance $N_2$

EXAMPLE 16

Pd—Bi—Rh—Ag on Steatite

Batches of 200 g of catalyst in the form of spheres having a diameter of 4-5 mm were prepared. 200 g of steatite spheres from Condea were placed without further pretreatment in a porcelain dish located on a shaking table. In accordance with the previously determined water uptake (the amount of water adhering externally to the spheres), 20 ml of a nitric acid solution of nitrates of the respective doping elements (active metals) were added to the shaken spheres. After 30 minutes, all spheres had been completely wetted. The spheres were subsequently dried at 80° C. under a nitrogen atmosphere for 16 hours and finally heated at 550° C. for 3 hours. Catalyst spheres having a very homogeneous and abrasion-resistant black metal shell covering their surface were obtained.

A catalyst having the composition $Pd_{0.6\%}Bi_{1.0\%}Rh_{1.33\%}Ag_{0.08\%}$/steatite, where the indices indicate the mass of the respective element, based on the weight of the support, in % by weight, was obtained.

EXAMPLE 17

Pd—Bi—Co on Steatite

The catalyst was prepared as described in Example 16. A catalyst having the composition $Pd_{1.5\%}Bi_{1.5\%}Co_{0.01\%}$/steatite was obtained.

EXAMPLES 18-20

Catalytic Activity Test 41 g (31 ml) of each of the catalysts from Examples 16 and 17 were tested in a salt bath reactor. The liquid output from the reactor comprised virtually exclusively 2-cyclopentenone and unreacted cyclopentanone. The by-product comprised mostly carbon dioxide. Unreacted cyclopentanone can be recirculated. The reaction conditions and the conversions and selectivities achieved are summarized in Table 11.

TABLE 11

|  | Example 18 | Example 19 | Example 20 |
|---|---|---|---|
| Composition | $Pd_{0.6\%}Bi_{1\%}Rh_{1.33\%}Ag_{0.08}$/ steatite | $Pd_{1.5\%}Bi_{1.5\%}Co_{0.01\%}$/ steatite | $Pd_{1.5\%}Bi_{1.5\%}Co_{0.01\%}$/ steatite |
| GHSV* | 7514 | 7514 | 3570 |
| Molar ratio of $O_2:N_2$:water vapor | 1:2:82:15 | 1:2:82:15 | 1:2:39:15 |
| Pressure | atmospheric pressure | atmospheric pressure | atmospheric pressure |
| Salt bath temperature [° C.] | 320 | 320 | 360 |
| Conversion | 50% | 51% | 49% |
| Selectivity | 37% | 62% | 56% |
| Yield | 19% | 31% | 27% |
| STY [g of cyclopentenone/(h * l of catalyst)] | 53 | 85 | 36 |

*Total space velocity (cyclopentanone + $O_2$ + $N_2$ + steam) in standard l/h per catalyst volume Figures for Examples 11 to 14

FIGS. 1 to 4 show (in each case plotted on the y axis) conversion (♦ [%]), selectivity of CRA formation (■ [%]) and CRA yield (▲ [%]) in the catalytic conversion of butyraldehyde into crotonaldehyde (CRA) achieved according to Examples 11 to 14 as a function of the (in each case plotted on the x axis) GHSV [$h^{-1}$] (FIG. 1), the oxygen partial pressure [%] (FIG. 2), the reaction temperature [° C.] (FIG. 3) and the water content [%] (FIG. 4).

EXAMPLE 21

Pd—Rh—Bi on Steatite (Total Loading: 3% by Weight)

5 g of steatite spheres (sieve fraction: from 0.5 to 1.0 mm, from Condea) which have been pretreated with aqueous NaOH are placed in a porcelain dish. A mixture of nitrates of the active metals is prepared in a container. The nitrates of the active metals are used as 1.0 mol/l solutions in 30% strength by weight. $HNO_3$.

The composition of the impregnation solution and of the catalyst prepared therewith (% by weight of active metal, based on the weight of the catalyst) is shown in Table 12 below.

TABLE 12

| Metal salts | Concentration [mol/l] | Amount [µl] | Concentration of active metal [% by weight] |
|---|---|---|---|
| $Pd(NO_3)_2 \cdot 2H_2O$ | 1.0 | 176.2 | 0.375 |
| $Rh(NO_3)_3 \cdot 2H_2O$ | 1.0 | 1093.2 | 2.25 |
| $Bi(NO_3)_3 \cdot 5H_2O$ | 1.0 | 89.7 | 0.375 |
| Water |  | 40.9 |  |

The solution (total of 1,400 µl, corresponding to the previously determined water uptake of the steatite support) is applied by means of a pipette to the steatite. The impregnated material is subsequently dried at 80° C. for 16 hours in a drying oven. It is then calcined at 550° C. in a nitrogen atmosphere for 3 hours in a muffle furnace.

EXAMPLE 22

Catalytic Activity Test 1 ml of the catalyst prepared in Example 21 is introduced into a stainless steel reactor and heated to the reaction temperature. Cyclohexanone is dehydrogenated to 2-cyclohexenone in the preheated reactor. Table 13 below shows the major process parameters (reaction temperature; space velocity over the catalyst (GHSV); composition of the feed gas mixture; cyclohexanone conversion; selectivity of 2-cyclohexenone formation; 2-cyclohexenone yield based on cyclohexanone). Analysis of the product gas mixture was carried out by means of GC/MS using an HP-5-MS column.

TABLE 13

| T [° C.] | GHSV [$h^{-1}$] | Cyclohexanone [% by volume] | $H_2O$ [% by volume] | $N_2$ [% by volume] | $O_2$ [% by volume] | Conversion [%] | Selectivity [%] | Yield [%] |
|---|---|---|---|---|---|---|---|---|
| 390 | 6000 | 4.0 | 10.0 | 78.0 | 8.0 | 67.9 | 62.2 | 42.9 |
| 420 | 6000 | 4.0 | 10.0 | 78.0 | 8.0 | 70.7 | 59.9 | 42.3 |
| 400 | 6000 | 4.0 | 10.0 | 78.0 | 8.0 | 70.5 | 59.1 | 41.7 |
| 410 | 6000 | 4.0 | 10.0 | 78.0 | 8.0 | 73.3 | 54.6 | 40.1 |
| 380 | 6000 | 4.0 | 10.0 | 78.0 | 8.0 | 73.8 | 49.9 | 36.9 |
| 390 | 6000 | 3.0 | 5.0 | 86.0 | 6.0 | 60.4 | 58.2 | 35.2 |
| 420 | 6000 | 3.0 | 5.0 | 86.0 | 6.0 | 57.2 | 59.1 | 33.8 |
| 410 | 6000 | 3.0 | 5.0 | 86.0 | 6.0 | 54.7 | 61.1 | 33.4 |
| 380 | 3000 | 3.0 | 5.0 | 86.0 | 6.0 | 63.5 | 50.8 | 32.2 |
| 400 | 6000 | 3.0 | 5.0 | 86.0 | 6.0 | 58.0 | 54.8 | 31.8 |
| 380 | 3000 | 3.0 | 5.0 | 84.0 | 8.0 | 73.8 | 42.7 | 31.5 |
| 380 | 3000 | 3.0 | 5.0 | 88.0 | 4.0 | 53.7 | 58.7 | 31.5 |

TABLE 13-continued

| T [° C.] | GHSV [h$^{-1}$] | Cyclohexanone [% by volume] | H$_2$O [% by volume] | N$_2$ [% by volume] | O$_2$ [% by volume] | Conversion [%] | Selectivity [%] | Yield [%] |
|---|---|---|---|---|---|---|---|---|
| 400 | 6000 | 4.0 | 10.0 | 83.0 | 3.0 | 39.4 | 77.2 | 30.4 |
| 380 | 6000 | 3.0 | 5.0 | 86.0 | 6.0 | 55.9 | 53.8 | 30.1 |
| 390 | 6000 | 4.0 | 10.0 | 83.0 | 3.0 | 34.2 | 86.6 | 29.6 |
| 380 | 6000 | 4.0 | 10.0 | 83.0 | 3.0 | 40.8 | 72.2 | 29.4 |
| 370 | 6000 | 4.0 | 10.0 | 83.0 | 3.0 | 36.7 | 78.2 | 28.7 |
| 360 | 6000 | 4.0 | 10.0 | 83.0 | 3.0 | 50.3 | 56.7 | 28.5 |

EXAMPLES 23 TO 132

Catalysts having different compositions were prepared in a manner analogous to Example 21 and their catalytic activity in the dehydrogenation of cyclohexanone to 2-cyclohexenone was tested in a manner analogous to Example 22. The catalyst composition, feed composition and conversion, selectivity and yield of the dehydrogenation of cyclohexanone to 2-cyclohexenone carried out using these catalysts are summarized in Table 14 below.

| Example No. | Catalyst composition | | | | Reaction conditions | | Feed composition [% by volume] | | | | Catalyst performance | | |
|---|---|---|---|---|---|---|---|---|---|---|---|---|---|
| | Pd [% by weight] | Rh [% by weight] | Bi [% by weight] | Pt [% by weight] | T [° C.] | GHSV [h$^{-1}$] | CH | H$_2$O | N$_2$ | O$_2$ | Conversion [%] | Selectivity [%] | Yield [%] |
| 23 | 0.45 | 2.1 | 0.45 | 0 | 420 | 3000 | 2 | 10 | 84 | 4 | 65.70 | 60.08 | 39.47 |
| 24 | 0.5 | 2 | 0.5 | 0 | 400 | 6000 | 3 | 10 | 81 | 6 | 62.13 | 62.3 | 38.75 |
| 25 | 0.45 | 2.1 | 0.45 | 0 | 400 | 3000 | 2 | 10 | 84 | 4 | 64.86 | 59.30 | 38.47 |
| 26 | 1.5 | 0.375 | 1.125 | 0 | 390 | 6000 | 3 | 0 | 92 | 5 | 57.94 | 65.59 | 38.00 |
| 27 | 1.2 | 0.6 | 1.2 | 0 | 420 | 6000 | 3 | 0 | 92 | 5 | 58.48 | 64.94 | 37.98 |
| 28 | 0.75 | 1 | 1.25 | 0.05 | 390 | 6000 | 3 | 0 | 92 | 5 | 56.49 | 66.84 | 37.76 |
| 29 | 0.75 | 1 | 1.25 | 0.05 | 420 | 6000 | 3 | 10 | 81 | 6 | 73.24 | 50.88 | 37.27 |
| 30 | 1.5 | 0.375 | 1.125 | 0 | 410 | 6000 | 3 | 0 | 92 | 5 | 57.02 | 65.34 | 37.26 |
| 31 | 0.5 | 2 | 0.5 | 0 | 420 | 3000 | 2 | 10 | 84 | 4 | 64.43 | 56.60 | 36.47 |
| 32 | 1.2 | 0.6 | 1.2 | 0 | 390 | 6000 | 3 | 0 | 92 | 5 | 58.49 | 61.89 | 36.20 |
| 33 | 0.5 | 2 | 0.5 | 0 | 400 | 3000 | 2 | 10 | 84 | 4 | 67.44 | 53.23 | 35.90 |
| 34 | 1.5 | 0.375 | 1.125 | 0 | 420 | 6000 | 3 | 0 | 92 | 5 | 59.18 | 60.47 | 35.78 |
| 35 | 1.2 | 0.6 | 1.2 | 0 | 410 | 6000 | 3 | 0 | 92 | 5 | 66.77 | 53.33 | 35.61 |
| 36 | 0.45 | 2.1 | 0.45 | 0 | 400 | 3000 | 3 | 0 | 91 | 6 | 60.09 | 59.21 | 35.58 |
| 37 | 0.5 | 2 | 0.5 | 0 | 420 | 6000 | 3 | 10 | 81 | 6 | 69.08 | 51.48 | 35.56 |
| 38 | 0.75 | 1 | 1.25 | 0.05 | 360 | 3000 | 2 | 10 | 84 | 4 | 55.75 | 63.62 | 35.47 |
| 39 | 1.5 | 0.375 | 1.125 | 0 | 380 | 6000 | 3 | 0 | 92 | 5 | 64.50 | 54.86 | 35.38 |
| 40 | 0.5 | 2 | 0.5 | 0 | 400 | 3000 | 3 | 0 | 91 | 6 | 62.07 | 56.90 | 35.32 |
| 41 | 0.75 | 1.5 | 0.75 | 0 | 390 | 6000 | 3 | 0 | 92 | 5 | 53.04 | 66.21 | 35.12 |
| 42 | 0.375 | 1.5 | 1.125 | 0 | 360 | 3000 | 2 | 10 | 84 | 4 | 53.86 | 64.83 | 34.92 |
| 43 | 0.5 | 2 | 0.5 | 0 | 380 | 6000 | 3 | 10 | 81 | 6 | 67.02 | 51.95 | 34.82 |
| 44 | 0.75 | 1 | 1.25 | 0.05 | 380 | 6000 | 3 | 10 | 81 | 6 | 71.70 | 48.35 | 34.67 |
| 45 | 1.5 | 0.375 | 1.125 | 0 | 420 | 6000 | 3 | 10 | 81 | 6 | 65.93 | 52.56 | 34.65 |
| 46 | 0.375 | 1.875 | 0.75 | 0 | 400 | 6000 | 3 | 10 | 81 | 6 | 58.03 | 59.71 | 34.65 |
| 47 | 1.5 | 0.375 | 1.125 | 0 | 400 | 6000 | 3 | 10 | 81 | 6 | 69.59 | 49.50 | 34.45 |
| 48 | 0.5 | 2 | 0.5 | 0 | 400 | 3000 | 2 | 10 | 82 | 6 | 79.42 | 43.38 | 34.45 |
| 49 | 1.2 | 0.6 | 1.2 | 0 | 400 | 6000 | 3 | 0 | 92 | 5 | 63.74 | 54.04 | 34.45 |
| 50 | 0.75 | 1.5 | 0.75 | 0 | 380 | 6000 | 3 | 0 | 92 | 5 | 53.63 | 63.95 | 34.30 |
| 51 | 0.5 | 2 | 0.5 | 0 | 360 | 3000 | 2 | 10 | 84 | 4 | 64.47 | 53.16 | 34.27 |
| 52 | 1.5 | 0 | 1.5 | 0 | 400 | 6000 | 3 | 10 | 81 | 6 | 58.63 | 58.38 | 34.23 |
| 53 | 0.45 | 2.1 | 0.45 | 0 | 420 | 6000 | 3 | 10 | 81 | 6 | 69.11 | 49.36 | 34.11 |
| 54 | 0.75 | 1 | 1.25 | 0.05 | 400 | 6000 | 3 | 10 | 81 | 6 | 73.94 | 46.07 | 34.07 |
| 55 | 0.375 | 2.25 | 0.375 | 0 | 420 | 6000 | 3 | 10 | 81 | 6 | 54.94 | 61.92 | 34.02 |
| 56 | 0.45 | 2.1 | 0.45 | 0 | 420 | 3000 | 3 | 0 | 91 | 6 | 63.2 | 53.82 | 34.02 |
| 57 | 1 | 1 | 1 | 0 | 400 | 3000 | 2 | 10 | 84 | 4 | 51.5 | 66.03 | 34.01 |
| 58 | 0.45 | 2.1 | 0.45 | 0 | 360 | 3000 | 2 | 10 | 84 | 4 | 62.36 | 54.47 | 33.96 |
| 59 | 1.2 | 0.6 | 1.2 | 0 | 420 | 6000 | 3 | 10 | 81 | 6 | 69.82 | 48.58 | 33.92 |
| 60 | 0.75 | 1.5 | 0.75 | 0 | 420 | 6000 | 3 | 0 | 92 | 5 | 57.28 | 59.17 | 33.89 |
| 61 | 1 | 0.25 | 1.75 | 0 | 380 | 6000 | 3 | 10 | 81 | 6 | 58.19 | 58.17 | 33.85 |
| 62 | 0.75 | 1.5 | 0.75 | 0 | 410 | 6000 | 3 | 0 | 92 | 5 | 62.55 | 53.85 | 33.68 |
| 63 | 0.75 | 1.875 | 0.375 | 0 | 400 | 6000 | 3 | 10 | 81 | 6 | 57.34 | 58.40 | 33.49 |
| 64 | 0.75 | 1 | 1.25 | 0.05 | 410 | 6000 | 3 | 0 | 92 | 5 | 59.22 | 56.54 | 33.48 |
| 65 | 1.5 | 0.375 | 1.125 | 0 | 400 | 6000 | 3 | 0 | 92 | 5 | 67.09 | 49.84 | 33.43 |
| 66 | 0.45 | 2.1 | 0.45 | 0 | 360 | 3000 | 2 | 10 | 82 | 6 | 70.43 | 47.45 | 33.42 |
| 67 | 0.25 | 1.75 | 1 | 0 | 400 | 3000 | 2 | 10 | 84 | 4 | 69.01 | 48.41 | 33.41 |
| 68 | 0.25 | 1.75 | 1 | 0 | 380 | 6000 | 3 | 10 | 81 | 6 | 60.24 | 55.37 | 33.36 |
| 69 | 0.25 | 1.75 | 1 | 0 | 380 | 3000 | 2 | 10 | 82 | 6 | 73.97 | 45.02 | 33.30 |

-continued

| Example No. | Catalyst composition | | | | Reaction conditions | | Feed composition [% by volume] | | | | Catalyst performance | | |
|---|---|---|---|---|---|---|---|---|---|---|---|---|---|
| | Pd [% by weight] | Rh [% by weight] | Bi [% by weight] | Pt [% by weight] | T [°C.] | GHSV [h$^{-1}$] | CH | H$_2$O | N$_2$ | O$_2$ | Conversion [%] | Selectivity [%] | Yield [%] |
| 70 | 0.375 | 1.5 | 1.125 | 0 | 420 | 3000 | 2 | 10 | 84 | 4 | 67.28 | 49.48 | 33.29 |
| 71 | 0.75 | 1 | 1.25 | 0.05 | 400 | 6000 | 3 | 0 | 92 | 5 | 63.89 | 52.05 | 33.25 |
| 72 | 0.6 | 1.8 | 0.6 | 0 | 380 | 6000 | 3 | 10 | 81 | 6 | 54.69 | 60.73 | 33.21 |
| 73 | 0.6 | 1.8 | 0.6 | 0 | 400 | 3000 | 2 | 10 | 84 | 4 | 62.29 | 53.16 | 33.12 |
| 74 | 0.75 | 1 | 1.25 | 0.05 | 420 | 6000 | 3 | 0 | 92 | 5 | 61.22 | 54.00 | 33.06 |
| 75 | 0.45 | 2.1 | 0.45 | 0 | 400 | 6000 | 3 | 10 | 81 | 6 | 65.06 | 50.81 | 33.05 |
| 76 | 1.5 | 0 | 1.5 | 0 | 360 | 3000 | 2 | 10 | 82 | 6 | 75.94 | 43.45 | 33.00 |
| 77 | 0.9 | 0.9 | 1.2 | 0 | 420 | 6000 | 3 | 0 | 92 | 5 | 56.20 | 58.48 | 32.87 |
| 78 | 1.5 | 0.375 | 1.125 | 0 | 360 | 6000 | 3 | 10 | 81 | 6 | 57.75 | 56.77 | 32.78 |
| 79 | 1.2 | 0.6 | 1.2 | 0 | 380 | 6000 | 3 | 0 | 92 | 5 | 56.96 | 57.50 | 32.76 |
| 80 | 0.5 | 2 | 0.5 | 0 | 420 | 3000 | 3 | 0 | 91 | 6 | 65.23 | 50.19 | 32.74 |
| 81 | 0.45 | 2.1 | 0.45 | 0 | 360 | 6000 | 3 | 10 | 81 | 6 | 59.46 | 55.05 | 32.73 |
| 82 | 1 | 1 | 1 | 0 | 360 | 3000 | 2 | 10 | 86 | 2 | 23.90 | 96.90 | 23.16 |
| 83 | 1.5 | 0 | 1.5 | 0 | 340 | 3000 | 2 | 10 | 86 | 2 | 28.32 | 96.89 | 27.44 |
| 84 | 1.5 | 0 | 1.5 | 0 | 360 | 3000 | 2 | 10 | 86 | 2 | 19.31 | 96.70 | 18.68 |
| 85 | 1.2 | 0.6 | 1.2 | 0 | 360 | 3000 | 2 | 10 | 86 | 2 | 25.09 | 95.92 | 24.07 |
| 86 | 1.8 | 0.15 | 1.05 | 0 | 360 | 3000 | 2 | 10 | 86 | 2 | 19.96 | 94.64 | 18.89 |
| 87 | 1.2 | 0.9 | 0.9 | 0 | 360 | 3000 | 2 | 10 | 86 | 2 | 17.77 | 93.67 | 16.65 |
| 88 | 1.8 | 0.6 | 0.6 | 0 | 390 | 6000 | 3 | 0 | 92 | 5 | 18.43 | 93.29 | 17.20 |
| 89 | 0.15 | 1.8 | 1.05 | 0 | 360 | 3000 | 2 | 10 | 86 | 2 | 25.84 | 92.48 | 23.90 |
| 90 | 1 | 1 | 1 | 0 | 390 | 6000 | 3 | 0 | 92 | 5 | 23.95 | 92.14 | 22.07 |
| 91 | 0.9 | 1.2 | 0.9 | 0 | 360 | 3000 | 2 | 10 | 86 | 2 | 24.99 | 92.10 | 23.02 |
| 92 | 0.25 | 0.25 | 2.5 | 0 | 400 | 6000 | 3 | 10 | 81 | 6 | 3.36 | 91.66 | 3.08 |
| 93 | 1.2 | 1.2 | 0.6 | 0 | 360 | 3000 | 2 | 10 | 86 | 2 | 17.36 | 90.72 | 15.75 |
| 94 | 2 | 0.5 | 0.5 | 0 | 380 | 6000 | 3 | 0 | 92 | 5 | 13.23 | 90.23 | 11.94 |
| 95 | 2.25 | 0 | 0.75 | 0 | 360 | 3000 | 2 | 10 | 86 | 2 | 16.97 | 89.99 | 15.27 |
| 96 | 0.15 | 0.15 | 2.7 | 0 | 340 | 3000 | 3 | 0 | 93 | 4 | 3.47 | 89.96 | 3.12 |
| 97 | 2.25 | 0.15 | 0.6 | 0 | 360 | 3000 | 2 | 10 | 86 | 2 | 13.28 | 89.79 | 11.92 |
| 98 | 0.75 | 1 | 1.25 | 0.05 | 360 | 3000 | 2 | 10 | 86 | 2 | 35.63 | 89.41 | 31.86 |
| 99 | 1.125 | 1.5 | 0.375 | 0 | 400 | 3000 | 2 | 10 | 86 | 2 | 21.60 | 89.16 | 19.26 |
| 100 | 0.15 | 0.15 | 2.7 | 0 | 380 | 6000 | 3 | 10 | 81 | 6 | 4.85 | 88.21 | 4.28 |
| 101 | 1.875 | 0.375 | 0.75 | 0 | 360 | 3000 | 2 | 10 | 86 | 2 | 14.55 | 87.81 | 12.77 |
| 102 | 1.5 | 0 | 1.5 | 0 | 360 | 3000 | 2 | 10 | 86 | 2 | 24.45 | 87.52 | 21.40 |
| 103 | 0.6 | 1.2 | 1.2 | 0 | 360 | 3000 | 2 | 10 | 86 | 2 | 26.82 | 87.14 | 23.38 |
| 104 | 0.15 | 0.15 | 2.7 | 0 | 360 | 3000 | 3 | 0 | 93 | 4 | 5.29 | 86.35 | 4.57 |
| 105 | 0.15 | 1.8 | 1.05 | 0 | 340 | 3000 | 2 | 10 | 86 | 2 | 25.99 | 85.68 | 22.26 |
| 106 | 1 | 1 | 1 | 0 | 410 | 6000 | 3 | 0 | 92 | 5 | 26.95 | 85.33 | 23.00 |
| 107 | 0.15 | 1.05 | 1.8 | 0 | 340 | 3000 | 2 | 10 | 86 | 2 | 14.82 | 85.15 | 12.62 |
| 108 | 1.2 | 1.2 | 0.6 | 0 | 380 | 3000 | 2 | 10 | 86 | 2 | 19.48 | 84.85 | 16.53 |
| 109 | 0.9 | 0.9 | 1.2 | 0 | 360 | 3000 | 2 | 10 | 86 | 2 | 34.38 | 83.87 | 28.83 |
| 110 | 0.6 | 0.15 | 2.25 | 0 | 340 | 3000 | 2 | 10 | 86 | 2 | 9.68 | 83.85 | 8.12 |
| 111 | 0.75 | 0 | 2.25 | 0 | 340 | 3000 | 2 | 10 | 86 | 2 | 12.26 | 83.77 | 10.27 |
| 112 | 0.5 | 0.5 | 2 | 0 | 360 | 3000 | 2 | 10 | 84 | 4 | 24.59 | 83.65 | 20.57 |
| 113 | 0.15 | 2.25 | 0.6 | 0 | 340 | 3000 | 2 | 10 | 86 | 2 | 29.52 | 83.20 | 24.56 |
| 114 | 0.375 | 0.375 | 2.25 | 0 | 340 | 3000 | 2 | 10 | 86 | 2 | 9.92 | 83.09 | 8.24 |
| 115 | 0.15 | 0.6 | 2.25 | 0 | 340 | 3000 | 2 | 10 | 86 | 2 | 9.38 | 82.08 | 7.70 |
| 116 | 0.9 | 0.9 | 1.2 | 0 | 380 | 3000 | 2 | 10 | 86 | 2 | 31.43 | 81.90 | 25.74 |
| 117 | 0.25 | 1.75 | 1 | 0 | 340 | 3000 | 2 | 10 | 86 | 2 | 34.43 | 81.89 | 28.19 |
| 118 | 0.375 | 1.125 | 1.5 | 0 | 340 | 3000 | 2 | 10 | 86 | 2 | 18.50 | 81.78 | 15.13 |
| 119 | 1.5 | 0.75 | 0.75 | 0 | 400 | 6000 | 3 | 0 | 92 | 5 | 19.51 | 80.92 | 15.79 |
| 120 | 0.15 | 1.05 | 1.8 | 0 | 340 | 3000 | 2 | 10 | 82 | 6 | 19.51 | 80.70 | 15.75 |
| 121 | 1.5 | 0.375 | 1.125 | 0 | 360 | 3000 | 2 | 10 | 86 | 2 | 29.30 | 79.61 | 23.33 |
| 122 | 1.5 | 0.375 | 1.125 | 0 | 380 | 3000 | 2 | 10 | 86 | 2 | 30.82 | 79.02 | 24.35 |
| 123 | 2.25 | 0.6 | 0.15 | 0 | 360 | 3000 | 2 | 10 | 86 | 2 | 7.68 | 78.86 | 6.06 |
| 124 | 0.15 | 0.15 | 2.7 | 0 | 340 | 3000 | 2 | 10 | 82 | 6 | 22.10 | 77.81 | 17.20 |
| 125 | 2.25 | 0.6 | 0.15 | 0 | 400 | 3000 | 2 | 10 | 84 | 4 | 13.60 | 77.79 | 10.58 |
| 126 | 1.8 | 0.15 | 1.05 | 0 | 360 | 3000 | 2 | 10 | 84 | 4 | 34.77 | 76.83 | 26.71 |
| 127 | 0.75 | 0.375 | 1.875 | 0 | 380 | 3000 | 2 | 10 | 86 | 2 | 27.75 | 76.38 | 21.19 |
| 128 | 0.75 | 1 | 1.25 | 0.05 | 340 | 3000 | 2 | 10 | 86 | 2 | 30.71 | 76.22 | 23.41 |
| 129 | 1 | 0.25 | 1.75 | 0 | 340 | 3000 | 2 | 10 | 86 | 2 | 27.96 | 76.14 | 21.29 |
| 130 | 0.375 | 1.875 | 0.75 | 0 | 340 | 3000 | 2 | 10 | 86 | 2 | 34.14 | 75.90 | 25.91 |
| 131 | 0.75 | 0.375 | 1.875 | 0 | 340 | 3000 | 2 | 10 | 86 | 2 | 17.70 | 75.65 | 13.39 |
| 132 | 0.375 | 1.875 | 0.75 | 0 | 380 | 3000 | 2 | 10 | 86 | 2 | 39.27 | 75.09 | 29.49 |

EXAMPLES 133 TO 281

Catalysts having different compositions were prepared in a manner analogous to Example 21 and their catalytic activity in the dehydrogenation of isovaleraldehyde to prenal was tested in a manner analogous to Example 22. The catalyst composition, feed composition and conversion, selectivity and yield of the dehydrogenation of isovaleraldehyde to 2-prenal carried out using these catalysts are summarized in Table 15 below.

| Ex-ample No. | Catalyst composition | | | | Reaction conditions | | Feed composition [% by volume] | | | | Catalyst performance | | |
|---|---|---|---|---|---|---|---|---|---|---|---|---|---|
| | Pd [% by weight] | Rh [% by weight] | Bi [% by weight] | Pt [% by weight] | T [°C.] | GHSV [h⁻¹] | CH | H₂O | N₂ | O₂ | Conversion [%] | Selectivity [%] | Yield [%] |
| 133 | 1.2 | 0.6 | 1.2 | 0 | 320 | 3000 | 2 | 20 | 64 | 14 | 56.76 | 21.38 | 12.14 |
| 134 | 1.2 | 0.6 | 1.2 | 0 | 320 | 3000 | 2 | 20 | 70 | 8 | 38.56 | 30.73 | 11.85 |
| 135 | 1.2 | 0.6 | 1.2 | 0 | 320 | 3000 | 22 | 20 | 66 | 12 | 59.87 | 18.79 | 11.25 |
| 136 | 1.2 | 0.6 | 1.2 | 0 | 320 | 3000 | 2 | 20 | 68 | 10 | 53.91 | 20.68 | 11.15 |
| 137 | 1.2 | 0.6 | 1.2 | 0 | 290 | 3000 | 2 | 20 | 70 | 8 | 29.08 | 37.58 | 10.93 |
| 138 | 1.2 | 0.6 | 1.2 | 0 | 300 | 3000 | 2 | 20 | 68 | 10 | 24.58 | 42.76 | 10.51 |
| 139 | 1.5 | 0.375 | 1.125 | 0 | 320 | 3000 | 2 | 20 | 64 | 14 | 50.71 | 20.40 | 10.35 |
| 140 | 1.2 | 0.6 | 1.2 | 0 | 310 | 3000 | 2 | 20 | 70 | 8 | 29.37 | 33.12 | 9.73 |
| 141 | 1.8 | 0.15 | 1.05 | 0 | 310 | 6000 | 3 | 20 | 70 | 8 | 38.35 | 25.32 | 9.71 |
| 142 | 1.2 | 0.6 | 1.2 | 0 | 320 | 3000 | 2 | 10 | 81 | 6 | 41.05 | 23.64 | 9.70 |
| 143 | 1.8 | 0.15 | 1.05 | 0 | 300 | 3000 | 2 | 20 | 70 | 8 | 30.88 | 31.24 | 9.65 |
| 144 | 1.8 | 0.15 | 1.05 | 0 | 300 | 3000 | 2 | 20 | 68 | 10 | 32.86 | 29.29 | 9.63 |
| 145 | 1.2 | 0.6 | 1.2 | 0 | 310 | 3000 | 2 | 20 | 64 | 14 | 41.41 | 23.03 | 9.53 |
| 146 | 1.8 | 0.15 | 1.05 | 0 | 310 | 3000 | 2 | 20 | 64 | 14 | 43.25 | 22.03 | 9.53 |
| 147 | 1.8 | 0.15 | 1.05 | 0 | 310 | 3000 | 2 | 20 | 70 | 8 | 41.22 | 23.07 | 9.51 |
| 148 | 1.5 | 0.375 | 1.125 | 0 | 320 | 3000 | 2 | 20 | 66 | 12 | 53.51 | 17.76 | 9.50 |
| 149 | 1.2 | 0.6 | 1.2 | 0 | 310 | 3000 | 2 | 20 | 66 | 12 | 44.34 | 21.06 | 9.34 |
| 150 | 1.2 | 0.6 | 1.2 | 0 | 310 | 3000 | 2 | 20 | 68 | 10 | 41.83 | 22.24 | 9.30 |
| 151 | 1.2 | 0.6 | 1.2 | 0 | 300 | 3000 | 2 | 20 | 64 | 14 | 27.55 | 33.77 | 9.30 |
| 152 | 1.8 | 0.15 | 1.05 | 0 | 310 | 3000 | 2 | 20 | 68 | 10 | 46.59 | 19.92 | 9.28 |
| 153 | 1.8 | 0.15 | 1.05 | 0 | 310 | 3000 | 2 | 20 | 66 | 12 | 45.73 | 20.27 | 9.27 |
| 154 | 1.8 | 0.15 | 1.05 | 0 | 320 | 3000 | 2 | 20 | 70 | 8 | 47.89 | 19.15 | 9.17 |
| 155 | 1.8 | 0.15 | 1.05 | 0 | 300 | 3000 | 2 | 20 | 66 | 12 | 34.30 | 26.65 | 9.14 |
| 156 | 0.75 | 1 | 1.25 | 0.05 | 290 | 6000 | 2 | 20 | 70 | 8 | 34.89 | 26.06 | 9.09 |
| 157 | 1.5 | 0.375 | 1.125 | 0 | 320 | 6000 | 2 | 20 | 70 | 8 | 42.62 | 21.25 | 9.06 |
| 158 | 1.5 | 0.375 | 1.125 | 0 | 310 | 3000 | 2 | 20 | 66 | 12 | 36.36 | 24.91 | 9.06 |
| 159 | 1.5 | 0.75 | 0.75 | 0 | 310 | 6000 | 2 | 20 | 70 | 8 | 31.47 | 28.72 | 9.04 |
| 160 | 1.5 | 0.75 | 0.75 | 0 | 320 | 6000 | 2 | 20 | 70 | 8 | 39.25 | 23.01 | 9.03 |
| 161 | 1.8 | 0.15 | 1.05 | 0 | 290 | 3000 | 2 | 20 | 70 | 8 | 30.52 | 29.44 | 8.99 |
| 162 | 1.8 | 0.15 | 1.05 | 0 | 300 | 3000 | 2 | 20 | 64 | 14 | 34.27 | 26.21 | 8.98 |
| 163 | 1.2 | 0.9 | 0.9 | 0 | 330 | 3000 | 4 | 10 | 81 | 5 | 40.04 | 22.19 | 8.89 |
| 164 | 1.5 | 0.375 | 1.125 | 0 | 320 | 3000 | 2 | 20 | 70 | 8 | 48.61 | 18.19 | 8.84 |
| 165 | 1.5 | 0.375 | 1.125 | 0 | 310 | 3000 | 2 | 20 | 64 | 14 | 37.35 | 23.48 | 8.77 |
| 166 | 1.8 | 0.15 | 1.05 | 0 | 320 | 6000 | 2 | 20 | 70 | 8 | 53.39 | 16.39 | 8.75 |
| 167 | 1.2 | 0.6 | 1.2 | 0 | 310 | 3000 | 3 | 10 | 81 | 6 | 30.50 | 28.55 | 8.71 |
| 168 | 1.5 | 0.375 | 1.125 | 0 | 310 | 3000 | 2 | 20 | 68 | 10 | 39.58 | 21.92 | 8.68 |
| 169 | 1.5 | 0.375 | 1.125 | 0 | 310 | 3000 | 2 | 20 | 70 | 8 | 36.42 | 23.82 | 8.67 |
| 170 | 1.2 | 0.9 | 0.9 | 0 | 320 | 6000 | 2 | 20 | 70 | 8 | 33.24 | 25.91 | 8.61 |
| 171 | 1.5 | 0.375 | 1.125 | 0 | 320 | 3000 | 2 | 20 | 68 | 10 | 53.73 | 16.00 | 8.59 |
| 172 | 1.75 | 0.25 | 1 | 0 | 310 | 3000 | 2 | 20 | 70 | 8 | 40.62 | 21.07 | 8.56 |
| 173 | 1.8 | 0.15 | 1.05 | 0 | 320 | 3000 | 2 | 20 | 66 | 12 | 54.14 | 15.80 | 8.55 |
| 174 | 1.5 | 0 | 1.5 | 0 | 310 | 3000 | 2 | 20 | 64 | 14 | 52.11 | 16.31 | 8.50 |
| 175 | 1.75 | 0.25 | 1 | 0 | 300 | 6000 | 2 | 20 | 70 | 8 | 29.59 | 28.09 | 8.31 |
| 176 | 1.2 | 0.6 | 1.2 | 0 | 300 | 3000 | 2 | 20 | 66 | 12 | 26.12 | 31.58 | 8.25 |
| 177 | 1.5 | 0.375 | 1.125 | 0 | 330 | 6000 | 2 | 20 | 70 | 8 | 57.49 | 14.33 | 8.24 |
| 178 | 1.5 | 0.375 | 1.125 | 0 | 300 | 3000 | 2 | 20 | 68 | 10 | 23.29 | 35.09 | 8.18 |
| 179 | 1.75 | 0.25 | 1 | 0 | 300 | 3000 | 2 | 20 | 70 | 8 | 37.46 | 21.72 | 8.14 |
| 180 | 0.9 | 0.9 | 1.2 | 0 | 320 | 3000 | 2 | 20 | 64 | 14 | 28.67 | 28.36 | 8.13 |
| 181 | 1.5 | 0.375 | 1.125 | 0 | 310 | 6000 | 2 | 20 | 70 | 8 | 23.27 | 34.91 | 8.12 |
| 182 | 1.5 | 0.375 | 1.125 | 0 | 290 | 3000 | 2 | 20 | 70 | 8 | 23.90 | 33.95 | 8.11 |
| 183 | 1.5 | 0.375 | 1.125 | 0 | 300 | 3000 | 2 | 20 | 70 | 8 | 25.80 | 31.31 | 8.08 |
| 184 | 1.5 | 0 | 1.5 | 0 | 330 | 6000 | 2 | 20 | 70 | 8 | 27.77 | 29.04 | 8.06 |
| 185 | 1.75 | 0.25 | 1 | 0 | 310 | 6000 | 2 | 20 | 70 | 8 | 46.87 | 17.20 | 8.06 |
| 186 | 0.9 | 0.9 | 1.2 | 0 | 310 | 3000 | 4 | 10 | 81 | 5 | 42.37 | 18.94 | 8.02 |
| 187 | 1.2 | 0.9 | 0.9 | 0 | 290 | 3000 | 2 | 20 | 70 | 8 | 22.91 | 34.91 | 8.00 |
| 188 | 1.5 | 0.375 | 1.125 | 0 | 300 | 3000 | 2 | 20 | 66 | 12 | 23.78 | 33.29 | 7.92 |
| 189 | 1.2 | 0.6 | 1.2 | 0 | 290 | 3000 | 2 | 20 | 68 | 10 | 26.88 | 29.38 | 7.90 |
| 190 | 1.2 | 0.6 | 1.2 | 0 | 330 | 3000 | 2 | 20 | 70 | 8 | 71.44 | 11.01 | 7.87 |
| 191 | 1.8 | 0.6 | 0.6 | 0 | 310 | 6000 | 2 | 20 | 70 | 8 | 23.23 | 33.48 | 7.78 |
| 192 | 0.6 | 1.2 | 1.2 | 0 | 290 | 3000 | 4 | 10 | 81 | 5 | 29.03 | 26.77 | 7.77 |
| 193 | 0.9 | 0.9 | 1.2 | 0 | 320 | 3000 | 2 | 20 | 66 | 12 | 29.21 | 26.59 | 7.77 |
| 194 | 1.75 | 0.25 | 1 | 0 | 310 | 3000 | 2 | 20 | 68 | 10 | 43.48 | 17.84 | 7.76 |
| 195 | 1.75 | 0.25 | 1 | 0 | 320 | 3000 | 2 | 20 | 70 | 8 | 56.09 | 13.81 | 7.75 |
| 196 | 0.9 | 0.9 | 1.2 | 0 | 320 | 3000 | 2 | 20 | 68 | 10 | 27.74 | 27.87 | 7.73 |
| 197 | 1.5 | 0 | 1.5 | 0 | 320 | 3000 | 2 | 20 | 66 | 12 | 50.32 | 15.36 | 7.73 |
| 198 | 0.9 | 0.9 | 1.2 | 0 | 330 | 3000 | 2 | 20 | 70 | 8 | 31.30 | 24.57 | 7.69 |
| 199 | 1.75 | 0.25 | 1 | 0 | 320 | 6000 | 2 | 20 | 70 | 8 | 57.21 | 13.35 | 7.64 |
| 200 | 0.9 | 1.2 | 0.9 | 0 | 290 | 3000 | 2 | 20 | 68 | 10 | 17.07 | 44.61 | 7.61 |
| 201 | 0.9 | 0.9 | 1.2 | 0 | 300 | 3000 | 4 | 10 | 81 | 5 | 35.68 | 21.27 | 7.59 |
| 202 | 2 | 0.5 | 0.5 | 0 | 320 | 6000 | 2 | 20 | 70 | 8 | 40.04 | 18.76 | 7.51 |
| 203 | 1.5 | 0 | 1.5 | 0 | 310 | 3000 | 2 | 20 | 64 | 14 | 36.40 | 20.60 | 7.50 |
| 204 | 1.5 | 0.375 | 1.125 | 0 | 300 | 3000 | 2 | 20 | 64 | 14 | 24.36 | 30.71 | 7.48 |

-continued

| Example No. | Catalyst composition | | | | Reaction conditions | | Feed composition [% by volume] | | | | Catalyst performance | | |
|---|---|---|---|---|---|---|---|---|---|---|---|---|---|
| | Pd [% by weight] | Rh [% by weight] | Bi [% by weight] | Pt [% by weight] | T [°C.] | GHSV [h⁻¹] | CH | H₂O | N₂ | O₂ | Conversion [%] | Selectivity [%] | Yield [%] |
| 205 | 0.6 | 1.2 | 1.2 | 0 | 310 | 3000 | 4 | 10 | 81 | 5 | 48.40 | 15.45 | 7.48 |
| 206 | 1.8 | 0.15 | 1.05 | 0 | 290 | 3000 | 2 | 20 | 68 | 10 | 28.05 | 26.52 | 7.44 |
| 207 | 1.5 | 0.75 | 0.75 | 0 | 300 | 6000 | 2 | 20 | 70 | 8 | 22.90 | 32.36 | 7.41 |
| 208 | 3 | 0 | 0 | 0 | 330 | 3000 | 4 | 10 | 81 | 5 | 42.04 | 17.61 | 7.40 |
| 209 | 1.5 | 0 | 1.5 | 0 | 290 | 3000 | 4 | 10 | 81 | 5 | 17.01 | 43.22 | 7.35 |
| 210 | 0.9 | 1.2 | 0.9 | 0 | 320 | 3000 | 2 | 20 | 66 | 12 | 31.92 | 22.94 | 7.32 |
| 211 | 0.9 | 0.9 | 1.2 | 0 | 330 | 3000 | 2 | 20 | 66 | 12 | 42.69 | 17.14 | 7.31 |
| 212 | 0.9 | 0.9 | 1.2 | 0 | 320 | 3000 | 2 | 20 | 70 | 8 | 22.97 | 31.74 | 7.29 |
| 213 | 1 | 1 | 1 | 0 | 320 | 3000 | 4 | 10 | 81 | 5 | 25.78 | 28.27 | 7.29 |
| 214 | 0.9 | 0.9 | 1.2 | 0 | 330 | 3000 | 2 | 20 | 64 | 14 | 47.70 | 15.25 | 7.27 |
| 215 | 1.75 | 0.25 | 1 | 0 | 310 | 3000 | 2 | 20 | 66 | 12 | 41.79 | 17.32 | 7.24 |
| 216 | 1.8 | 0.15 | 1.05 | 0 | 290 | 3000 | 2 | 20 | 64 | 14 | 27.38 | 26.38 | 7.22 |
| 217 | 1 | 1 | 1 | 0 | 300 | 3000 | 4 | 10 | 81 | 5 | 13.50 | 53.26 | 7.19 |
| 218 | 1 | 1 | 1 | 0 | 320 | 3000 | 4 | 10 | 81 | 5 | 35.08 | 20.48 | 7.18 |
| 219 | 1.75 | 0.25 | 1 | 0 | 290 | 3000 | 2 | 20 | 70 | 8 | 32.20 | 22.25 | 7.17 |
| 220 | 1.5 | 0 | 1.5 | 0 | 320 | 3000 | 2 | 20 | 68 | 10 | 49.15 | 14.45 | 7.10 |
| 221 | 1.2 | 0.6 | 1.2 | 0 | 330 | 3000 | 3 | 10 | 81 | 6 | 59.64 | 11.87 | 7.08 |
| 222 | 0.9 | 0.9 | 1.2 | 0 | 330 | 3000 | 4 | 10 | 81 | 5 | 39.13 | 18.02 | 7.05 |
| 223 | 1.8 | 0.15 | 1.05 | 0 | 330 | 3000 | 2 | 20 | 64 | 14 | 73.01 | 9.66 | 7.05 |
| 224 | 0.9 | 0.9 | 1.2 | 0 | 310 | 3000 | 2 | 20 | 64 | 14 | 23.36 | 30.10 | 7.03 |
| 225 | 1.5 | 0.375 | 1.125 | 0 | 290 | 3000 | 2 | 20 | 66 | 12 | 23.84 | 29.38 | 7.01 |
| 226 | 1.5 | 0 | 1.5 | 0 | 290 | 3000 | 2 | 20 | 70 | 8 | 34.76 | 20.13 | 7.00 |
| 227 | 0.9 | 0.9 | 1.2 | 0 | 290 | 3000 | 4 | 10 | 81 | 5 | 7.01 | 99.49 | 6.98 |
| 228 | 1.5 | 0 | 1.5 | 0 | 320 | 3000 | 2 | 20 | 66 | 12 | 66.77 | 10.44 | 6.97 |
| 229 | 0.9 | 0.9 | 1.2 | 0 | 310 | 3000 | 2 | 20 | 66 | 12 | 21.38 | 32.61 | 6.97 |
| 230 | 1.875 | 0.375 | 0.75 | 0 | 310 | 6000 | 2 | 20 | 70 | 8 | 28.74 | 24.25 | 6.97 |
| 231 | 1.5 | 0 | 1.5 | 0 | 320 | 3000 | 2 | 20 | 64 | 14 | 63.96 | 10.86 | 6.95 |
| 232 | 1 | 1 | 1 | 0 | 330 | 3000 | 4 | 10 | 81 | 5 | 18.87 | 36.81 | 6.94 |
| 233 | 1.2 | 0.9 | 0.9 | 0 | 290 | 3000 | 4 | 10 | 81 | 5 | 8.88 | 77.87 | 6.92 |
| 234 | 0.75 | 1.5 | 0.75 | 0 | 320 | 6000 | 2 | 20 | 70 | 8 | 26.01 | 26.51 | 6.90 |
| 235 | 2.1 | 0.45 | 0.45 | 0 | 320 | 6000 | 2 | 20 | 70 | 8 | 33.76 | 20.27 | 6.84 |
| 236 | 1.8 | 0.15 | 1.05 | 0 | 290 | 3000 | 4 | 10 | 81 | 5 | 26.42 | 25.78 | 6.81 |
| 237 | 1.5 | 0 | 1.5 | 0 | 320 | 3000 | 2 | 20 | 64 | 14 | 50.51 | 13.42 | 6.78 |
| 238 | 1.5 | 0 | 1.5 | 0 | 310 | 3000 | 2 | 20 | 66 | 12 | 60.12 | 11.23 | 6.75 |
| 239 | 0.9 | 1.2 | 0.9 | 0 | 290 | 3000 | 4 | 10 | 81 | 5 | 12.23 | 55.03 | 6.73 |
| 240 | 0.9 | 0.9 | 1.2 | 0 | 290 | 3000 | 2 | 20 | 70 | 8 | 12.47 | 53.69 | 6.70 |
| 241 | 0.9 | 0.9 | 1.2 | 0 | 330 | 3000 | 2 | 20 | 68 | 10 | 42.85 | 15.62 | 6.69 |
| 242 | 0.9 | 0.9 | 1.2 | 0 | 310 | 3000 | 2 | 20 | 68 | 10 | 25.91 | 25.83 | 6.69 |
| 243 | 1.8 | 0.15 | 1.05 | 0 | 330 | 3000 | 2 | 20 | 70 | 8 | 66.01 | 10.06 | 6.64 |
| 244 | 1.8 | 0.15 | 1.05 | 0 | 300 | 6000 | 2 | 20 | 70 | 8 | 21.40 | 30.93 | 6.62 |
| 245 | 1.2 | 0.6 | 1.2 | 0 | 300 | 3000 | 2 | 20 | 70 | 8 | 20.27 | 32.58 | 6.60 |
| 246 | 1.5 | 0 | 1.5 | 0 | 310 | 3000 | 2 | 20 | 68 | 10 | 41.95 | 15.72 | 6.60 |
| 247 | 1.2 | 0.9 | 0.9 | 0 | 300 | 3000 | 4 | 10 | 81 | 5 | 17.34 | 37.93 | 6.58 |
| 248 | 1.2 | 0.6 | 1.2 | 0 | 290 | 3000 | 2 | 20 | 66 | 12 | 26.31 | 24.90 | 6.55 |
| 249 | 1.5 | 0.75 | 0.75 | 0 | 330 | 6000 | 2 | 20 | 70 | 8 | 54.84 | 11.87 | 6.51 |
| 250 | 1.8 | 0.15 | 1.05 | 0 | 290 | 3000 | 2 | 20 | 66 | 12 | 30.16 | 21.54 | 6.49 |
| 251 | 1 | 1 | 1 | 0 | 300 | 3000 | 4 | 10 | 81 | 5 | 17.96 | 36.09 | 6.48 |
| 252 | 1.5 | 0.75 | 0.75 | 0 | 290 | 3000 | 2 | 20 | 70 | 8 | 18.92 | 34.22 | 6.47 |
| 253 | 1.75 | 0.25 | 1 | 0 | 290 | 3000 | 2 | 20 | 68 | 10 | 30.03 | 21.47 | 6.45 |
| 254 | 1 | 1 | 1 | 0 | 300 | 3000 | 3 | 10 | 81 | 6 | 36.34 | 17.74 | 6.45 |
| 255 | 0.9 | 0.9 | 1.2 | 0 | 310 | 3000 | 2 | 20 | 70 | 8 | 18.05 | 35.58 | 6.42 |
| 256 | 1 | 1 | 1 | 0 | 310 | 3000 | 3 | 10 | 81 | 6 | 35.17 | 18.17 | 6.39 |
| 257 | 0.75 | 1.5 | 0.75 | 0 | 330 | 6000 | 2 | 20 | 70 | 8 | 37.68 | 16.93 | 6.38 |
| 258 | 1.5 | 0.75 | 0.75 | 0 | 290 | 3000 | 4 | 10 | 81 | 5 | 17.64 | 36.13 | 6.37 |
| 259 | 2.1 | 0.45 | 0.45 | 0 | 310 | 6000 | 2 | 20 | 70 | 8 | 23.20 | 27.35 | 6.35 |
| 260 | 1.5 | 0.375 | 1.125 | 0 | 310 | 3000 | 3 | 10 | 81 | 6 | 31.03 | 20.41 | 6.33 |
| 261 | 0.75 | 1 | 1.25 | 0.05 | 330 | 3000 | 4 | 10 | 81 | 5 | 33.32 | 18.97 | 6.32 |
| 262 | 1 | 1 | 1 | 0 | 290 | 3000 | 4 | 10 | 81 | 5 | 10.71 | 58.98 | 6.32 |
| 263 | 0.9 | 0.9 | 1.2 | 0 | 290 | 3000 | 2 | 20 | 68 | 10 | 11.89 | 52.54 | 6.25 |
| 264 | 0.75 | 1.5 | 0.75 | 0 | 310 | 6000 | 2 | 20 | 70 | 8 | 18.99 | 32.82 | 6.23 |
| 265 | 1.8 | 0.15 | 1.05 | 0 | 330 | 3000 | 2 | 20 | 66 | 12 | 74.55 | 8.35 | 6.22 |
| 266 | 0.6 | 1.2 | 1.2 | 0 | 300 | 3000 | 4 | 10 | 81 | 5 | 48.60 | 12.80 | 6.22 |
| 267 | 1.2 | 1.2 | 0.6 | 0 | 310 | 6000 | 2 | 20 | 70 | 8 | 27.67 | 22.47 | 6.22 |
| 268 | 0.9 | 1.2 | 0.9 | 0 | 290 | 3000 | 2 | 20 | 70 | 8 | 22.97 | 27.03 | 6.21 |
| 269 | 1.75 | 0.25 | 1 | 0 | 310 | 3000 | 2 | 20 | 64 | 14 | 48.02 | 12.92 | 6.20 |
| 270 | 1 | 1 | 1 | 0 | 290 | 3000 | 4 | 10 | 81 | 5 | 6.40 | 96.66 | 6.19 |
| 271 | 1.8 | 0.6 | 0.6 | 0 | 300 | 6000 | 2 | 20 | 70 | 8 | 20.33 | 30.40 | 6.18 |
| 272 | 1.875 | 0.375 | 0.75 | 0 | 300 | 6000 | 2 | 20 | 70 | 8 | 29.77 | 20.55 | 6.12 |
| 273 | 0.9 | 1.2 | 0.9 | 0 | 290 | 3000 | 3 | 10 | 81 | 6 | 16.80 | 36.40 | 6.11 |
| 274 | 1.5 | 0.75 | 0.75 | 0 | 310 | 3000 | 4 | 10 | 81 | 5 | 34.50 | 17.70 | 6.11 |
| 275 | 1.2 | 1.2 | 0.6 | 0 | 320 | 6000 | 2 | 20 | 70 | 8 | 24.29 | 25.14 | 6.11 |
| 276 | 1 | 1 | 1 | 0 | 320 | 3000 | 3 | 10 | 81 | 6 | 39.55 | 15.38 | 6.08 |

-continued

| Example No. | Catalyst composition | | | | Reaction conditions | | Feed composition [% by volume] | | | | Catalyst performance | | |
|---|---|---|---|---|---|---|---|---|---|---|---|---|---|
| | Pd [% by weight] | Rh [% by weight] | Bi [% by weight] | Pt [% by weight] | T [°C.] | GHSV [h$^{-1}$] | CH | H$_2$O | N$_2$ | O$_2$ | Conversion [%] | Selectivity [%] | Yield [%] |
| 277 | 1.5 | 0 | 1.5 | 0 | 310 | 3000 | 2 | 20 | 66 | 12 | 46.22 | 13.15 | 6.08 |
| 278 | 1.2 | 1.2 | 0.6 | 0 | 300 | 3000 | 4 | 10 | 81 | 5 | 19.51 | 30.87 | 6.02 |
| 279 | 1.8 | 0.6 | 0.6 | 0 | 320 | 6000 | 2 | 20 | 70 | 8 | 34.10 | 17.66 | 6.02 |
| 280 | 0.9 | 1.2 | 0.9 | 0 | 320 | 3000 | 2 | 20 | 64 | 14 | 33.60 | 17.85 | 6.00 |
| 281 | 0.75 | 1 | 1.25 | 0.05 | 290 | 3000 | 4 | 10 | 81 | 5 | 28.48 | 21.05 | 6.00 |

We claim:

1. A method of dehydrogenation of cyclic or acyclic carbonyl compounds to the corresponding α,β-unsaturated carbonyl compounds comprising contacting a catalytically active composition comprising an active component of the formula $Pd_aBi_cY_d$ wherein Y=Au or Rh, and wherein the indices a, c and d indicate the mass ratios of the respective elements and $0.1 \leq a \leq 3$, $0.1 \leq c \leq 3$ and $0 \leq d \leq 1$, on silicon carbide or steatite as carrier with cyclic or acyclic carbonyl compounds to produce the corresponding α,β-unsaturated carbonyl compounds.

2. The method according to claim 1 wherein the cyclic or acyclic carbonyl compound is selected from the group consisting of cyclopentanone, butanone, butyraldehyde, cyclohexanone and isovaleraldehyde.

3. A method of dehydrogenation of cyclic or acyclic carbonyl compounds to the corresponding α,β-unsaturated carbonyl compounds comprising contacting a catalytically active composition comprising an active component of the formula $Pd_aRh_bBi_c$ wherein the indices a, b, c indicate the mass ratios of the respective elements and $0.1 \leq a \leq 3$, $0 \leq b \leq 3$ and $0.1 \leq c \leq 3$, on silicon carbide or steatite as carrier with cyclic or acyclic carbonyl compounds to produce the corresponding α,β-unsaturated carbonyl compounds.

4. The method according to claim 3, wherein the cyclic or acyclic carbonyl compound is selected from the group consisting of cyclopentanone, butanone, butyraldehyde, cyclohexanone and isovaleraldehyde.

5. A method of dehydrogenation of cyclic or acyclic carbonyl compounds to the corresponding α,β-unsaturated carbonyl compounds comprising contacting a catalytically active composition comprising an active component of the formula $Pd_aBi_c$, wherein a and c indicate the mass ratios of the respective elements and $0.1 \leq a \leq 3$ and $0.1 \leq c \leq 3$, on silicon carbide or steatite as carrier with cyclic or acyclic carbonyl compounds to produce the corresponding α,β-unsaturated carbonyl compounds.

6. The method according to claim 5, wherein the cyclic or acyclic carbonyl compounds are selected from the group consisting of cyclopentanone, butanone, butyraldehyde, cyclohexanone and isovaleraldehyde.

7. A method of dehydrogenation of cyclic or acyclic carbonyl compounds to the corresponding α,β-unsaturated carbonyl compounds comprising contacting a catalytically active composition comprising an active component of the formula $Pd_aRh_bBi_cZ_e$ wherein Z=Ag or Pt, and wherein the indices a, b, c and e indicate the mass ratios of the respective elements and $0.1 \leq a \leq 3$, $0 \leq b \leq 3$, $0.1 \leq c \leq 3$ and $0 \leq e \leq 1$, on silicon carbide or steatite as carrier with cyclic or acyclic carbonyl compounds to produce the corresponding α,β-unsaturated carbonyl compounds.

8. The method according to claim 7, wherein the cyclic or acyclic carbonyl compounds are selected from the group consisting of cyclopentanone, butanone, butyraldehyde, cyclohexanone and isovaleraldehyde.

9. A method of dehydrogenation of cyclic or acyclic carbonyl compounds to the corresponding α,β-unsaturated carbonyl compounds comprising contacting a catalytically active composition comprising an active component of the formula $Pd_aBi_cCo_e$ wherein the indices a, c and e indicate the mass ratios of the respective elements and $0.1 \leq a \leq 3$, $0.1 \leq c \leq 3$ and $0 \leq e \leq 1$, on silicon carbide or steatite as carrier with cyclic or acyclic carbonyl compounds to produce the corresponding α,β-unsaturated carbonyl compounds.

10. The method according to claim 9, wherein the cyclic or acyclic carbonyl compounds are selected from the group consisting of cyclopentanone, butanone, butyraldehyde, cyclohexanone and isovaleraldehyde.

11. A method of dehydrogenation of cyclic or acyclic carbonyl compounds to the corresponding α,β-unsaturated carbonyl compounds comprising contacting a catalytically active composition comprising an active component having a formula selected from the group consisting of:

$Pd_{0.5-1.0}Rh_{0.5-1.25}Bi_{1.25-1.75}Ag_{0.05-0.15}$ $Pd_{0.5-1.0}Rh_{1.0-1.5}Bi_{0.75-1.25}Pt_{0.01-0.1}$ $Pd_{0.25-0.5}Rh_{1.75-2.5}Bi_{0.25-0.5}Co_{0.01-0.1}$ $Pd_{0.5-1.25}Rh_{0.5-1.25}Bi_{0.75-1.5}Cr_{0.01-0.1}$ $Pd_{1.0-1.75}Rh_{0.25-0.75}Bi_{0.75-1.5}Pt_{0.0-0.15}Co_{0.01-0.1}$ $Pd_{1.0-1.75}Rh_{0.25-0.75}Bi_{0.75-1.5}Pt_{0.05-0.15}$ $Pd_{0.5-1.0}Rh_{1.0-1.75}Bi_{0.5-1.25}Ag_{0.03-0.15}Ca_{0.02-0.1}$ $Pd_{0.4-1.0}Rh_{1.0-1.75}Bi_{0.75-1.25}Ag_{0.03-0.15}$ $Pd_{1.25-1.75}Bi_{1.25-1.75}Co_{0.005-0.02}$ $Pd_{0.4-1.0}Rh_{1.0-1.75}Bi_{0.75-1.25}$ and $Pd_{0.15-2.25}Rh_{0-2.5}Bi_{0.15-2.75}$ on a carrier with cyclic or acyclic carbonyl compounds to produce the corresponding α,β-unsaturated carbonyl compounds.

12. The method according to claim 11, wherein the cyclic or acyclic carbonyl compounds are selected from the group consisting of cyclopentanone, butanone, butyraldehyde, cyclohexanone and isovaleraldehyde.

* * * * *